(12) United States Patent
Blackstock et al.

(10) Patent No.: US 7,270,962 B2
(45) Date of Patent: Sep. 18, 2007

(54) METHOD OF IDENTIFYING MODULATORS OF NOGO-FUNCTIONS

(75) Inventors: Walter Philip Blackstock, Stevenage (GB); Richard Stephen Hale, Stevenage (GB); Rabinder Prinjha, Harlow (GB); Adele Rowley, Stevenage (GB)

(73) Assignees: Glaxo Group Limited, Greenford (GB); SmithKline Beecham plc, Brentford (GB)

( * ) Notice: Subject to any disclaimer, the term of this patent is extended or adjusted under 35 U.S.C. 154(b) by 472 days.

(21) Appl. No.: 10/466,258

(22) PCT Filed: Jan. 18, 2002

(86) PCT No.: PCT/GB02/00228

§ 371 (c)(1),
(2), (4) Date: Feb. 4, 2004

(87) PCT Pub. No.: WO02/057483

PCT Pub. Date: Jul. 25, 2002

(65) Prior Publication Data

US 2004/0132096 A1    Jul. 8, 2004

(30) Foreign Application Priority Data

Jan. 18, 2002  (GB) ................. 0101312.7

(51) Int. Cl.
| | |
|---|---|
| *G01N 33/53* | (2006.01) |
| *A61K 38/00* | (2006.01) |
| *A61K 49/00* | (2006.01) |
| *C07K 14/00* | (2006.01) |
| *C07K 5/00* | (2006.01) |
| *C07K 16/00* | (2006.01) |

(52) U.S. Cl. ................... 435/7.1; 514/2; 424/9.2; 530/350; 530/300; 530/388.22

(58) Field of Classification Search ............ None
See application file for complete search history.

(56) References Cited

FOREIGN PATENT DOCUMENTS

| | | |
|---|---|---|
| WO | WO 00/31235 | 6/2000 |
| WO | WO 00/69262 | 11/2000 |
| WO | WO 01/51520 | 7/2001 |
| WO | WO 02/058323 | 7/2002 |

OTHER PUBLICATIONS

He, et al, 2004, Nature Medicine, 10(9):959-965.*
Cadelli et al., "Oligodendrocyte- and myelin-associated inhibitors of neurite outgrowth: their involvement in the lack of CNS regeneration," *Experimental Neurology* 115:189-192 (1992).
Hussain et al., "Identification of a novel aspartic protease (Asp 2) as β-secretase," *Molecular and Cellular Neuroscience* 14:419-427 (1999).
Kitazume et al., "Alzheimer's beta-secretase, beta-site amyloid precursor protein-cleaving enzyme, is responsible for cleavage secretion of a Golgi-resident sialyltransferase," *Proc. Nat'l. Acad. Sci. USA* 98(24):13554-13559 (Nov. 2001).
Sinha et al., "Purification and cloning of amyloid precursor protein β-secretase from human brain," *Nature* 402(6761):537-540 (Dec. 1999).
Vassar et al., "β-secretase cleavage of Alzheimer's amyloid precursor protein by the transmembrane aspartic protease BACE," *Science* 286(5440):735-741 (Oct. 1999).
Yan et al., "Membrane-anchored aspartyl protease with Alzheimer's disease β-secretase activity," *Nature* 402(6761):533-537 (Dec. 1999).

* cited by examiner

*Primary Examiner*—Eileen B. O'Hara
*Assistant Examiner*—Sandra Wegert
(74) *Attorney, Agent, or Firm*—Virginia G. Campen

(57) ABSTRACT

A method of identifying a modulator Nogo function, the method comprising:
  (i) providing
    (a) a BACE polypeptide;
    (b) a Nogo polypeptide;
    (c) a test agent
under conditions that would permit binding of a BACE polypeptide (a) to a Nogo polypeptide (b) in the absence of the test agent (c) wherein said BACE polypeptide (a) is BACE or a variant thereof or a fragment of either thereof capable of binding Nogo; and polypeptide (b) is Nogo or a variant thereof or a fragment of either thereof capable of binding BACE;
  (ii) monitoring Nogo mediated activity; and
  (iii) determining thereby whether the test agent is a modulator of Nogo activity.
Modulators identified by a method of the invention and use of such modulators in the manufacture of a medicament for the treatment of disorders responsive to the modulation of Nogo activity such as acute neuronal injury.

8 Claims, 11 Drawing Sheets

US 7,270,962 B2

METHOD OF IDENTIFYING MODULATORS OF NOGO-FUNCTIONS

This application is filed pursuant to 35 U.S.C. § 371 as a United States National Phase Application of International Application No. PCT/GB02/00228 filed Jan. 18, 2002, which claims priority from Great Britain Application No. 0101312.7 filed in the United Kingdom on Jan. 18, 2001.

FIELD OF THE INVENTION

This invention relates to methods of identifying modulators of Nogo and/or BACE activity and their use in the treatment of conditions which are responsive to modulation of Nogo activity such as acute neuronal injury.

BACKGROUND TO THE INVENTION

At least three Nogo isoforms are generated by alternative splicing of transcripts derived form the NogoA gene. The C-terminal third of all three isoforms shares high homology (approximately 70% at the amino acid level) with the reticulon protein family. NogoA, the largest isoform, has been shown to inhibit axon regeneration in culture. It is thought that the normal role of Nogo proteins is to prevent axon sprouting in the uninjured central nervous system. NogoA is localised to central nervous system myelin and is highly expressed in oligodendrocytes; NogoB and NogoC are expressed in some neurons and several non-neural tissues. All Nogo isoforms surprisingly have a C-terminal ER-retention motif but at least some NogoA protein is thought to reach the cell surface. All 3 Nogo isoforms have 2 potential trans-membrane domains. Both the C and N termini may be cytoplasmically exposed and a 66 amino acid loop separated by the TM domains may be located extracellularly.

An aspartyl protease called BACE (also known as Asp2 or memapsin2) has recently been shown to be responsible for β-secretase activity in relation to amyloid precursor protein (APP) processing. BACE is a type I transmembrane protein with a large lumenal domain containing the protease domain.

SUMMARY OF THE INVENTION

The present inventors have identified a novel interaction between Nogo and BACE. The interaction between Nogo and BACE provides a new therapeutic intervention point in disorders involving defective NOGO function and more specifically in acute neronal injury such as spinal injury, stroke, head injury and peripheral nerve damage, neoplastic disease, hyperproliferative disorders and dysproliferative disorders. In addition, BACE is now proposed as a target for identifying agents which may be useful in the treatment of acute neuronal injury, neoplastic disorders, hyperproliferative disorders and dysproliferative disorders.

Accordingly the invention provides a method of identifying a modulator NOGO function, the method comprising:
(i) providing
  (a) a BACE polypeptide
  (b) a Nogo polypeptide
  (c) a test agent
under conditions that would permit binding of a BACE polypeptide (a) to a Nogo polypeptide (b) in the absence of the test agent (c) and wherein said BACE polypeptide (a) is BACE or a variant thereof or a fragment of either thereof capable of binding Nogo and said Nogo polypeptide (b) is Nogo or a variant thereof or a fragment of either thereof capable of binding BACE.
(ii) monitoring Nogo mediated activity; and
(iii) determining thereby whether the test agent is a modulator of Nogo activity.

In a further aspect, the invention provides a method for identification of a modulator of BACE activity, which method comprises:
(i) contacting BACE or a variant thereof or a fragment of either thereof which maintains a BACE function with a test agent; and
(ii) monitoring for BACE activity
thereby determining whether the test agent is a modulator of BACE activity.

The invention also provides:
a modulator identifiable by a method according to the invention;
use of a modulator identifiable by a method according to the invention in the manufacture of a medicament for the treatment or prophylaxis of acute neuronal injury, neoplastic disorders, hyperproliferative disorders or dysproliferative disorders;
use of a BACE polypeptide or a polynucleotide encoding a BACE polypeptide in the manufacture of a medicament for the treatment of acute neuronal injury, neoplasia, hyperproliferative disorders or dysproliferative disorders wherein said BACE polypeptide is BACE or a variant thereof or fragment of either thereof which is capable of binding Nogo;
a method of treatment of acute neuronal injury, neoplasia, hyperproliferative disorders or dysproliferative disorders comprising administering an effective amount of a BACE polypeptide, a polynucleotide encoding a BACE polypeptide or a modulator of BACE function identified by a method of the invention to a human or animal in need of such treatment wherein said BACE polypeptide is BACE or a variant thereof or fragment of either thereof which variant or fragment is capable of binding Nogo; and
a method of treatment of acute neuronal injury, neoplasia, hyperproliferative disorders or dysproliferative disorders comprising:
(i) identifying a modulator of BACE activity; and
(ii) administering a therapeutically effective amount of the said modulator to a patient in need thereof.

BRIEF DESCRIPTION OF THE SEQUENCES

Figure 1A:
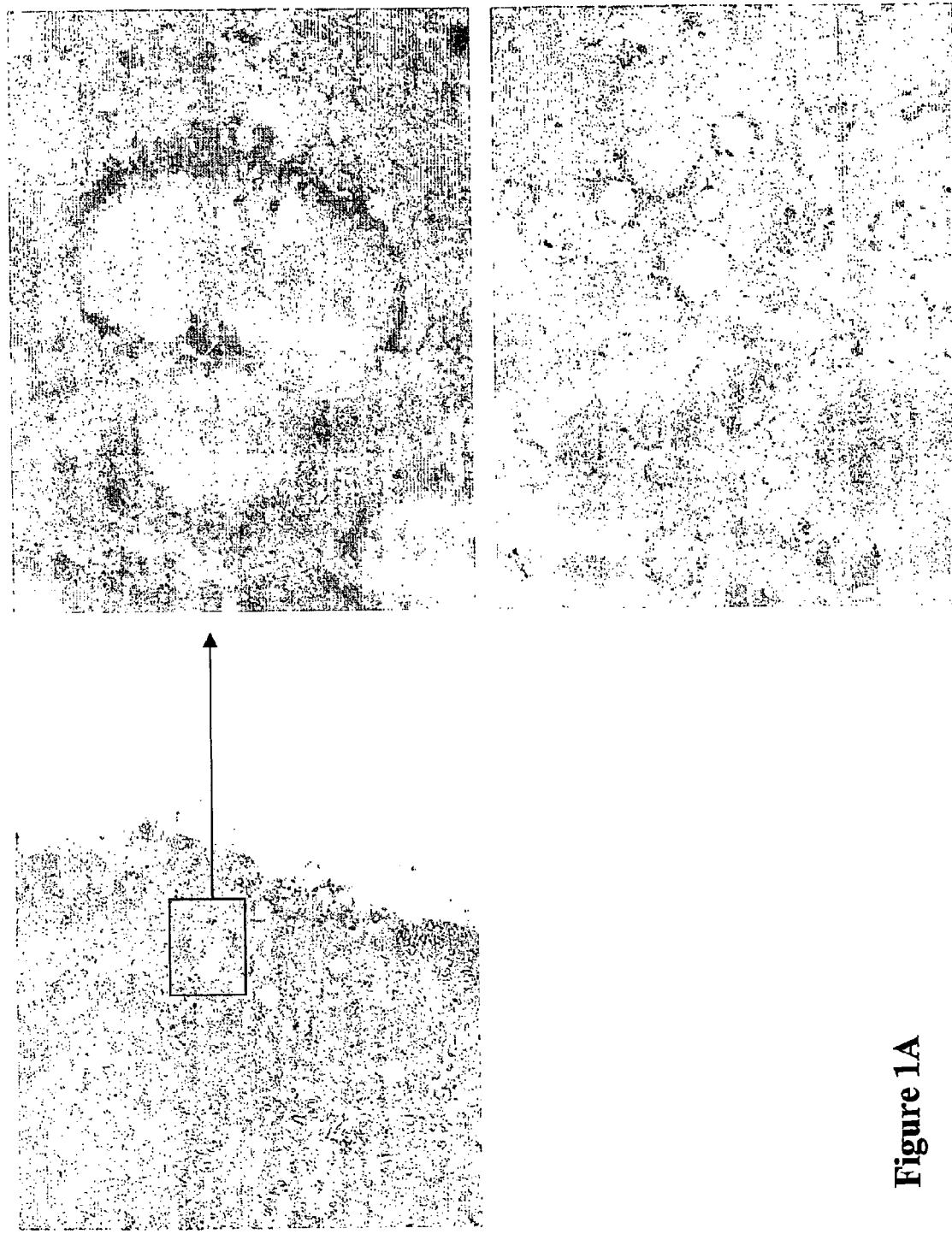
FIG. 1A Tas10 (mouse #4) sections stained with Nogo-A monoclonal antibody (6D5). Note presence of a ring of staining surrounding plaques of all sizes.

SEQ ID No: 1 shows the BACE nucleotide coding sequence and amino acid sequence.

SEQ ID No: 2 is the amino acid sequence of BACE.

SEQ ID No: 3 shows the NogoB nucleotide coding sequence and amino acid sequence.

SEQ ID No: 4 is the amino acid sequence of NogoB.

SEQ ID No: 5 is an amino acid fragment of NogoB identified in an assay to identify proteins which bind BACE.

SEQ ID No: 6 is an amino acid fragment of NogoB identified in an assay to identify proteins which bind BACE.

SEQ ID No: 7 is an amino acid fragment of NogoB identified in an assay to identify proteins which bind BACE.

SEQ ID No: 8 shows the NogoA nucleotide coding sequence and amino acid sequence.

SEQ ID No: 9 is the amino acid sequence of NogoA.

SEQ ID No: 10 shows the NogoC nucleotide coding sequence and amino acid sequence.

SEQ ID No: 11 is the amino acid sequence of NogoC.

SEQ ID No: 12 shows the BACE2 nucleotide coding sequence and amino acid sequence.

SEQ ID No: 13 is the amino acid sequence of BACE2.

DETAILED DESCRIPTION OF THE INVENTION

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows.

The invention provides a method for identifying a modulator of Nogo activity and a method for identifying a modulator of BACE activity. A modulator may modulate the interaction between Nogo and BACE.

A Nogo polypeptide for use in accordance with the invention is one which capable of binding BACE. The Nogo polypeptide may be NogoA, (accession number AJ251383), NogoB (accession number AB015639) or NogoC (accession number AF125103). The Nogo polypeptide comprises the amino acid sequence of SEQ ID No: 4, 9 or 11 or a functional variant or functional fragment thereof. The Nogo polypeptide preferably comprises the amino acid sequence of SEQ ID No: 4 or a functional variant or a functional fragment thereof. A variant may comprise a naturally occurring isoform or splice variant. A variant or fragment of SEQ ID No: 4, 9 or 11 for use in accordance with the invention is capable of binding to BACE. Particularly preferred variants of Nogo include other members of the reticulon protein family. Particularly preferred fragments and variants of SEQ ID No: 4 comprise the amino acid sequence shown in SEQ ID No: 5, 6 and/or 7.

A BACE polypeptide for use in accordance with the may comprise a naturally occurring BACE such as BACE (accession numbers AF190725, P56817) having the amino acid sequence of SEQ ID No: 1 or SEQ ID No: 2 or may comprise a variant or fragment of BACE which may be a naturally occurring BACE such as BACE2 (accession numbers AF204944, Q9Y5Z0) having the amino acid sequence of SEQ ID No: 12 or SEQ ID No: 13 or another unidentified isoform or splice variant which is homologous to or retains the desired function of a known BACE. Such a variant or fragment of BACE for use in the invention is one which is capable of binding to a Nogo polypeptide, in particular to a Nogo polypeptide having the sequence of SEQ ID No: 5, 6 or 7. Preferably a variant or fragment of BACE is capable of binding to full length NogoA, NogoB and/or NogoC. A preferred variant or a preferred fragment of BACE may also comprise an aspartyl protease active site. Such preferred variants and fragments retain the ability to cleave proteins and peptides comprising a β-secretase cleavage site. Preferably such variants and fragments encompass amino acid residues 93 to 96 (DTGS) and/or residues 289-292 (DSGT) of SEQ ID No: 2 or residues 109-112 (DTGS) and/or 300-303 (DSGT) of SEQ ID No: 13.

To determine whether a variant or fragment of BACE is capable of binding to Nogo the variant or fragment can be contacted with Nogo under conditions suitable for the formation of a complex between BACE and Nogo. Similarly, to determine whether a variant or fragment of Nogo is capable of binding to BACE, the variant or fragment can be contacted with BACE under conditions suitable for the formation of a complex between Nogo and BACE. Any one of the assays described herein can be carried out in the absence of a test agent to determine the binding capabilities of these proteins.

Proteins with naturally occurring amino acid sequences are preferred for use in the assays. Preferred proteins are human proteins but homologues from other mammalian species, or other animal species may be used. Any allelic variant or species homologue of the defined proteins may be used. References to a variant or fragment of the protein as described below relates to a variant or fragment of both Nogo and BACE. For all the proteins described herein for use in an assay of the invention, the ability of the variant or fragment to bind BACE or Nogo as appropriate is preferably maintained.

Polypeptides that have been artificially mutated but retain BACE or Nogo binding activity or other Nogo or BACE activity may also be used in the invention. Such mutants may be generated by techniques well known in the art, including site directed mutagenesis, random mutagenesis and restriction enzyme digestion and ligation. A protein for use in the invention preferably has more than about 65% sequence identity to a natural protein, more preferably at least 70%, at least 80%, at least 90%, at least 95%, at least 97% or at least 99% sequence identity thereto over a region of at least 20, preferably at least 30, for instance at least 40, at least 60 or at least 100 contiguous amino acids or over the full length of SEQ ID No: 2 or 13 or SEQ ID No: 4, 9 or 11. Amino acid substitutions may be made, for example from 1, 2 or 3 to 10, 20 or 30 substitutions. Conservative substitutions may be made, for example according to the following Table. Amino acids in the same block in the second column and preferably in the same line in the third column may be substituted for each other.

| ALIPHATIC | Non-polar | G A P |
|---|---|---|
|  |  | I L V |
|  | Polar-uncharged | C S T M |
|  |  | N Q |
|  | Polar-charged | D E |
|  |  | K R |
| AROMATIC |  | H F W Y |

The entire protein sequence of each of the proteins used in the assay may be present. Fragments of the proteins and variants described above that retain the ability to bind to the second component in the binding assay, i.e. BACE for Nogo polypeptides and Nogo for BACE polypeptides may also be used in the invention. Alternatively variants or fragments of BACE which retain a function of BACE may be used in assays to identify modulators of BACE activity. Preferred fragments of SEQ ID No: 2 will be at least 30, e.g. at least 100, at least 200, at least 300, at least 400 or at least 450 amino acids in length. Preferred fragments of SEQ ID No: 4 will be at least 30, e.g. at least 100, at least 200 or at least 250 amino acids in length. A fragment may comprise part of a polypeptide, for example a chimeric polypeptide. A chimeric protein may be used to facilitate the purification of a BACE or Nogo polypeptide. For example, the lumenal domain of BACE (amino acids 1 to 460 of SEQ ID No: 2) may be fused to human IgG at the carboxy-terminus.

As used herein, a Nogo polypeptide (a) is used to refer to Nogo having the sequence of SEQ ID No: 4, 9 or 11 or a variant thereof or a fragment of either thereof which variant or fragment is capable of binding to BACE, or to a variant or a fragment of BACE which is capable of binding to Nogo.

As used herein, a BACE polypeptide (a) is used to refer to BACE having the sequence of SEQ ID No: 2 or 13 or a variant thereof or a fragment of either thereof which variant or fragment is capable of binding to Nogo, or to a variant or a fragment of Nogo which is capable of binding to BACE.

The polypeptides for use in the invention may be chemically modified, e.g. post-translationally modified. For example, they may be glycosylated or comprise modified amino acid residues. The polypeptides may be tagged to aid detection or purification, for example using a HA, histidine, T7, myc or flag tag. The BACE polypeptide (a) and the Nogo polypeptide (b) may be tagged with different labels which may assist in identification of a BACE/Nogo complex.

Assays

Any suitable assay format may be used for identifying a modulator of a Nogo activity, for example a modulator of a BACE/Nogo interaction.

As the first step of the method for identifying a modulator of Nogo function, (a) a BACE polypeptide comprising the sequence of SEQ ID No: 2 or 13 or a variant thereof or a fragment of either sequence capable of binding to Nogo; (b) a Nogo polypeptide comprising the sequence of SEQ ID No: 4, 9 or 11 or a variant thereof or a fragment of either sequence capable of binding to BACE; and (c) a test agent are contacted under conditions that would permit binding of (a) to (b) in the absence of a test agent. An activity of Nogo is then monitored. For example, the interaction between the BACE polypeptide (a) and the Nogo polypeptide (b) may be analysed. The interaction between the BACE polypeptide (a) and the Nogo polypeptide (b) in the presence of a test agent may be compared with the interaction between the BACE polypeptide (a) and the Nogo polypeptide (b) in the absence of the test agent to determine whether the test agent modulates the binding of BACE polypeptide (a) and the Nogo polypeptide (b) and thereby whether the test agent enhances or inhibits the binding BACE to Nogo.

The test agent can be contacted with a cell harbouring a polynucleotide or expression vector encoding a BACE polypeptide (a) and a polynucleotide or expression vector encoding a Nogo polypeptide (b). Optionally, the cell may harbour a polynucleotide or expression vector encoding a test agent, wherein the test agent is a peptide or an antisense polynucleotide. The cell typically allows transcription and translation of the polynucleotides or vectors so that the polypeptides are expressed in the same cell.

The test agent may be provided in the extracellular medium used for washing, incubating or growing the cell. The test agent may modulate the interaction of the Nogo polypeptide (b) with the BACE polypeptide (a) indirectly from outside the cell, for example by interacting with an extracellular domain of BACE or Nogo or may be taken up into the cell from the extracellular medium. Where the BACE polypeptide (a) and the Nogo polypeptide (b) are coexpressed in a cell, the cell may express both proteins naturally, for example the cell may be a neuronal cell grown in a primary culture, or the cell may express both proteins recombinantly, or the cell may naturally express one protein and be transformed to express the other protein recombinantly.

The cell may be transiently or stably transfected or transformed. The BACE polypeptide (a) and the Nogo polypeptide (b) may both be transiently expressed, both stably expressed or one may be stably expressed and the other transiently expressed. Cells can be transfected by methods well known in the art, for example, by electroporation, calcium phosphate precipitation, lipofection or heat shock. The proteins may be expressed in mammalian cells such as human cells or non-mammalian cells such as yeast or bacteria. It is preferred that the cells are in culture. Preferred cell lines which may be used include HEK293, COS and PC12 cells.

A cell expressing a BACE polypeptide (a) or a cell homogenate, a cell lysate, a membrane preparation or a protein preparation derived from a cell expressing a BACE polypeptide (a) can be contacted with a cell expressing a Nogo polypeptide (b) or a cell homogenate, a cell lysate, a membrane preparation or a protein preparation derived from cells expressing a Nogo polypeptide (b).

The conditions which permit binding of a BACE polypeptide (a) to a Nogo polypeptide (b) in an extracellular environment can be determined by carrying out the assay in the absence of a test agent.

A control assay in which the agent to be tested is omitted and an assay in which a test agent is included can be carried out in parallel or subsequently. The results of the experiments using the test agent and the control experiments can be used to determine whether the test agent inhibits or enhances binding.

The agent tested may be tested with any other known interacting protein combinations to exclude the possibility that the test agent is a general inhibitor of protein/protein interactions.

Where the BACE polypeptide (a) used in the assay is a variant or fragment of SEQ ID No: 2 or 13, or the Nogo polypeptide (b) used in the assay is a variant or fragment of SEQ ID No: 4, 9 or 11, the assay is preferably run first in the absence of a test agent to ensure that the variant or fragment exhibits the activity being monitored, such as binding activity or protease activity.

A number of biochemical and molecular cell biology protocols known in the art can be used to analyse the interaction of a BACE polypeptide (a) and a Nogo polypeptide (b) (see for example Sambrook et al., 1989). Some specific examples are outlined below:

The BACE/Nogo interaction can be determined directly using a binding assay. For example, a radiolabelled BACE polypeptide (a) may be incubated with a Nogo polypeptide (b) in the presence and absence of the test agent and the effect of the test agent on the binding of the BACE polypeptide (a) to the Nogo polypeptide (b) is monitored. Typically, the radiolabelled BACE polypeptide (a) is incubated with cell membranes containing the Nogo polypeptide (b) until equilibrium is reached. The membranes can then be separated from non-bound radiolabelled BACE polypeptide (a) and dissolved in scintillation fluid to allow the radioactive content to be determined by scintillation counting. Non-specific binding of the agent may also be determined by repeating the experiment in the presence of a saturating concentration of a non-radioactive BACE polypeptide (a). Preferably a binding curve is constructed by repeating the experiment with various concentrations of the radiolabelled BACE polypeptide, both in the presence and absence of the test agent.

A yeast-2 hybrid assay system may be used to monitor the effect of a test agent on the BACE/Nogo interaction. For example, a polynucleotide encoding a BACE polypeptide (a) can be cloned into GAL4 binding domain vector ($GAL4_{BD}$) and a Nogo polynucleotide (b) can be cloned into a GAL4 activation domain fusion vector ($GAL4_{AD}$). The $GAL4_{AD}$ and $GAL4_{BD}$ vectors can then be expressed in yeast and the resulting Ǝ-galactosidase activity in the presence and absence of the test agent can be assayed and quantified using the substrate o-nitrophenol Ǝ-D-galactopyranoside (ONPG) using a liquid nitrogen freeze fracture regime as described by Harshman et al., 1998.

A "pull-down" assay system may also be used. Isolated BACE polypeptide (a) may be immobilised on a surface and binding of a Nogo polypeptide (b) to the surface may be monitored in the presence and absence of the test agent. The assay can also be carried out by immobilizing a Nogo polypeptide (b) and measuring the binding of a BACE polypeptide (a) to the immobilized protein.

Alternatively, of a BACE polypeptide (a) may be immunoprecipitated, immunopurified or affinity purified from a cell extract of cells co-expressing a BACE polypeptide (a) and a Nogo polypeptide (b). Coprecipitating/copurifying Nogo polypeptide (b) can then be detected, for example using Western blotting techniques or by radiolabelling recombinantly expressed proteins, and quantified using a phosphorimager or scintillation counter. The test agent is generally added to the cells or the cell growth medium prior to preparation of the cell lysate. Such assays may also be carried out by precipitating or purifying a Nogo polypeptide (b) and detecting coprecipitating or copurifying BACE polypeptide (a).

The assays may also be carried out monitoring other Nogo functions. For example, the neurite inhibitory activity of Nogo may be monitored. Neurite inhibitory activity may be monitored using any suitable assay format such as a dorsal root ganlion (DRG) neurite outgrowth assay, a DRG growth cone collapse assay, a neuronal cell line (for example, PC12 cell) neurite outgrowth assay or a fibroblast (such as NIH 3T3) cell spreading assay. For example, neurite outgrowth in the presence of a cell expressing BACE and Nogo may be monitored and the ability of a test agent to inhibit or promote neurite outgrowth may be assayed. To determine whether the effect of the test agent on neurite growth results from the effect of the test agent on BACE activity or on the BACE/Nogo interaction, a control assay may be carried out using cells expressing Nogo but not BACE. Typically, the cell will also express one or more neurotrophic factors.

An important aspect of the present invention is the use of a BACE polypeptide (a) in screening methods to identify agents that may act as modulators of BACE activity and in particular agents that may be useful in treating Nogo associated disease. Any suitable form may be used for the assay to identify a modulator of BACE activity. In general terms, such screening methods may involve contacting BACE polypeptide (a) with a test agent and then measuring activity. For example, the step of monitoring BACE activity may involve assessment of BACE protease activity, for example by cleaving a peptide comprising the β-secretase cleavage site (SEVKM/DAEFR or SEVNL/DAEFR) or the effect of binding of BACE to other proteins. For example the assay may involve determination of APP processing as described in Vassar et al. (1999) Science 286, 735-741, Hussain et al. (1999) Molecular and Cellular Neuroscience 14, 419-427, Sinha et al. (1999) Nature 402, 537-540 or Yan et al. (1999) Nature 402, 533-537.

Modulator activity can be determined by contacting cells expressing a BACE polypeptide (a) of the invention with an agent under investigation and monitoring the effect of the agent on BACE activity. The cells expressing the polypeptide may be in vitro or in vivo. The polypeptide of the invention may be naturally or recombinantly expressed. Preferably, the assay is carried out in vitro using cells expressing recombinant polypeptide.

Candidate Modulators

A modulator of Nogo or BACE function may exert its effect by binding directly to Nogo or BACE or may have an upstream effect which prevents the BACE/Nogo interaction occurring or which inhibits Nogo or BACE mediated activity.

A modulator may directly inhibit the interaction of Nogo with BACE or inhibit interaction between BACE and a ligand. A test agent may comprise a fragment of a BACE which is capable of binding Nogo or a BACE ligand but which lacks any functional activity. Alternatively, a test agent may comprise a fragment of Nogo which is capable of binding BACE but which lacks any functional activity.

Antibodies, or antibody fragments that specifically bind to BACE or Nogo or chemical compounds capable of binding these proteins are also candidate compounds. An antibody, or other compound, "specifically binds" to a protein when it binds with high affinity to the protein for which it is specific but does not bind or binds with only low affinity to other proteins. A variety of protocols for competitive binding or immunoradiometric assays to determine the specific binding capability of an antibody are well known in the art (see for example Maddox et al. 1993). Such immunoassays typically involve the formation of complexes between the "specific protein" and its antibody and the measurement of complex formation.

Furthermore, combinatorial libraries, defined chemical identities, peptide and peptide mimetics, oligonucleotides and natural product libraries, such as display libraries (e.g. phage display libraries) may also be tested. The test agents may be chemical compounds. Batches of the test agents may be used in an initial screen of, for example, ten agents per reaction, and the agents of batches which show inhibition tested individually.

Modulators

A modulator of Nogo activity is an agent which produces a measurable reduction or increase in binding of a Nogo polypeptide (b) to BACE polypeptide (a) in the assays described above, or an effect on Nogo activity or BACE activity.

Preferred inhibitors are those which inhibit binding by at least 10%, at least 20%, at least 30%, at least 40% at least 50%, at least 60%, at least 70%, at least 80%, at least 90%, at least 95% or at least 99% at a concentration of the inhibitor of 1 µg ml$^{-1}$, 10 µg ml$^{-1}$, 100 µg ml$^{-1}$, 500 µg ml$^{-1}$, 1 mg ml$^{-1}$, 10 mg ml$^{-1}$ or 100 mg ml$^{-1}$.

Preferred activators are those which activate binding by at least 10%, at least 25%, at least 50%, at least 100%, at least, 200%, at least 500% or at least 1000% at a concentration of the activator 1 µg ml$^{-1}$, 10 µg ml$^{-1}$, 100 µg ml$^{-1}$, 500 µg ml$^{-1}$, 1 mg ml$^{-1}$, 10 mg ml$^{-1}$ or 100 mg ml$^{-1}$.

The percentage inhibition or activation represents the percentage decrease or increase in expression/activity in a comparison of assays in the presence and absence of the test agent. Any combination of the above mentioned degrees of percentage inhibition or activation and concentration of inhibitor or activator may be used to define an inhibitor or activator of the invention, with greater inhibition or activation at lower concentrations being preferred.

Test agents which show activity in assays such as those described above can be tested in in vivo systems, an animal model. Candidate inhibitors could be tested for their ability to decrease Nogo mediated signalling, for example by monitoring the effect on axon growth.

Candidate activators could be tested for their ability to increase Nogo mediated signalling. Ultimately such agents would be tested in animal models of the target disease states.

Therapeutic Use

Modulators of the interaction between BACE and Nogo or of Nogo activity or of BACE activity identified by the methods of the invention may be used for the treatment or prophylaxis of a disorder that is responsive to modulation of Nogo activity or BACE activity.

In particular, neuronal disorders that are responsive to modulation of BACE and/or Nogo activity may be treated. A modulator of Nogo or BACE activity may be used to alleviate the symptoms or to improve the condition of a patient suffering from such a disorder.

Modulators of Nogo or BACE activity may be useful in axon regeneration. This may be useful in treating patients suffering injury to the nervous system, and in particular to the spinal cord, brain, for example following stroke, and peripheral nervous system. Such modulators will typically inhibit Nogo activity, for example by inhibiting the inhibitory effect of Nogo on axon regeneration.

Modulators of Nogo or BACE activity may be useful in treating or preventing neoplastic disorders, hyperproliferative disorders and dysproliferative disorders. In particular neoplastic disorders of the nervous system such as solid tumours, carcinomas, glioblastomas, oligodendrogliomas, neuroblastomas and retinoblastomas may be treated or prevented using modulators of Nogo or BACE activity. Hyperproliferative disorders and dysproliferative disorders that may be treated with a modulator of Nogo or BACE function include cirrhosis of the liver, psoraisis, benign tumours, keloid formation, fibrocystic conditions and tissue hypertrophy. Such modulators will typically enhance or promote Nogo activity, for example by promoting the inhibitory effect of Nogo on axon regeneration.

Modulators of Nogo or BACE activity may be useful in preventing metastasis or spreading of a cancer. For example, an agent which promotes the inhibitory activity of Nogo may be useful for preventing spreading of a CNS cancer to other organs of the body, such as lung, kidney, liver or muscle.

BACE polypeptides and polynucleotides encoding BACE polypeptides may also be used in the treatment or prophylaxis of such disorders.

The invention therefore provides a use of a polynucleotide which encodes BACE or a variant thereof which is capable of binding Nogo or a fragment of either thereof which is capable of binding Nogo, which polynucleotide comprises:

(a) the sequence of SEQ ID No: 1 or 12; or
(b) a sequence that hybridizes to the complement of SEQ ID No: 1 or 12; or
(c) a sequence that is degenerate as a result of the genetic code with respect to a sequence defined in (a) or (b); or
(d) a sequence that is complementary to a polynucleotide defined in (a), (b) or (c);

in the manufacture of a medicament for use in a method of treatment of a disorder that is responsive to modulation of Nogo activity.

A polynucleotide comprising a sequence that hybridizes to the complement of the coding sequence of SEQ ID No: 1 or 12 can hydridize at a level significantly above background. Background hybridization may occur, for example, because of other cDNAs present in a cDNA library. The signal level generated by the interaction between a polynucleotide of the invention and the complement of the coding sequence of SEQ ID No: 1 or 12 is typically at least 10 fold, preferably at least 100 fold, as intense as interactions between other polynucleotides and the coding sequence of SEQ ID No: 1 or 12. The intensity of interaction may be measured, for example, by radiolabelling the probe, e.g. with $^{32}$P. Selective hybridisation may typically be achieved using conditions of low stringency (0.3M sodium chloride and 0.03M sodium citrate at about 40° C.), medium stringency (for example, 0.3M sodium chloride and 0.03M sodium citrate at about 50° C.) or high stringency (for example, 0.03M sodium chloride and 0.003M sodium citrate at about 60° C.). However, such hybridization may be carried out under any suitable conditions known in the art (see Sambrook et al., 1989). For example, if high stringency is required, suitable conditions include 0.2×SSC at 60° C. If lower stringency is required, suitable conditions include 2×SSC at 60° C.

A nucleotide sequence which is capable of selectively hybridizing to the complement of the DNA coding sequence of SEQ ID No: 1 or 12 will generally have at least 60%, at least 70%, at least 80%, at least 90%, at least 95%, at least 98% or at least 99% sequence identity to the coding sequence of SEQ ID No: 1 over a region of at least 20, preferably at least 30, for instance at least 40, at least 60, more preferably at least 100 contiguous nucleotides or most preferably over the full length of SEQ ID No: 1 or 12. Methods of measuring nucleic acid and protein homology are well known in the art. For example the UWGCG Package provides the BESTFIT program which can be used to calculate homology (Devereux et al., 1984). Similarly, the PILEUP and BLAST algorithms can be used to line up sequences (for example as described in Altschul, 1993 and Altschul et al., 1990.) Many different settings are possible for such programs. According to the invention, the default settings may be used.

Any combination of the above mentioned degrees of sequence identity and minimum sizes may be used to define polynucleotides encoding a BACE polypeptide, with the more stringent combinations (i.e. higher sequence identity over longer lengths) being preferred. Thus, for example a polynucleotide which has at least 90% sequence identity over 25, preferably over 30 nucleotides forms one aspect of the invention, as does a polynucleotide which has at least 95% sequence identity over 40 nucleotides.

The coding sequence of SEQ ID No: 1 or 12 may be modified by nucleotide substitutions, for example from 1, 2 or 3 to 10, 25, 50 or 100 substitutions. The polynucleotide of SEQ ID No: 2 or 13 may alternatively or additionally be modified by one or more insertions and/or deletions and/or by an extension at either or both ends. The modified polynucleotide generally encodes a protein that can bind Nogo. Typically the protein encoded by the modified polypeptide has aspartyl protease activity. Degenerate substitutions may be made and/or substitutions may be made which would result in a conservative amino acid substitution when the modified sequence is translated, for example as shown in the Table above.

Polynucleotides may comprise DNA or RNA. They may also be polynucleotides which include within them synthetic or modified nucleotides. A number of different types of modification to polynucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or lifespan of polynucleotides of the invention.

Polynucleotides encoding a BACE polypeptide may be produced recombinantly, synthetically, or by any means available to those of skill in the art. They may also be cloned by standard techniques. The polynucleotides are typically provided in isolated and/or purified form.

Although in general the techniques mentioned herein are well known in the art, reference may be made in particular to Sambrook et al, 1989, Molecular Cloning: a laboratory manual.

A polynucleotide may also be an essential component in an assay of the invention, a probe (or template for designing a probe) for identifying proteins that may be used in the invention or a test agent. The nucleotides may be involved in recombinant protein synthesis as well as therapeutic agents in their own right, utilised in gene therapy techniques. Antisense sequences, may also be used in gene therapy, such as in strategies for down regulation of expression of BACE.

Polynucleotides for use in the invention can be inserted into expression vectors. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for protein expression. Other suitable vectors would be apparent to persons skilled in the art. By way of further example in this regard we refer to Sambrook et al.

Polynucleotides may also be inserted into the vectors described above in an antisense orientation in order to provide for the production of antisense RNA. Antisense RNA or other antisense polynucleotides may also be produced by synthetic means. Such antisense polynucleotides may be used as test compounds in the assays of the invention or may be useful in a method of treatment of a disorder responsive to modulation of Nogo activity, in particular for the treatment of injury to the spinal cord or peripheral nervous system.

Examples of suitable viral vectors include herpes simplex viral vectors and retroviruses, including lentiviruses, adenoviruses, adeno-associated viruses and HPV viruses (such as HPV-16 or HPV-18). Gene transfer techniques using these viruses are known to those skilled in the art. Retrovirus vectors for example may be used to stably integrate the polynucleotide giving rise to the antisense RNA into the host genome. Replication-defective adenovirus vectors by contrast remain episomal and therefore allow transient expression.

The formulation of an agent for use in preventing or treating any of the above mentioned conditions will depend upon factors such as the nature of the agent identified, whether a pharmaceutical or veterinary use is intended, etc. Typically a modulator is formulated for use with a pharmaceutically acceptable carrier or diluent. For example it may be formulated for topical, parenteral, intravenous, intramuscular, subcutaneous, intraocular, transdermal or oral administration. A physician will be able to determine the required route of administration for each particular patient. The pharmaceutical carrier or diluent may be, for example, an isotonic solution.

The dose of an agent may be determined according to various parameters, especially according to the agent used; the age, weight and condition of the patient to be treated; the route of administration; and the required regimen. Again, a physician will be able to determine the required route of administration and dosage for any particular patient.

Modulators may have to be administered to specific sites, or otherwise targeted to brain cells. For example, the modulator may be delivered to neurons. This may be achieved, for example, by delivery via a viral strain such as herpes simplex virus. Viral vectors comprising polynucleotides of the invention are described above. The viral vector delivery method may be used in the case of administration of, for example, polynucleotides of the invention. The vector may further comprise a promoter or other regulatory sequence that is specific to certain neurons.

The polynucleotides and vectors of the invention may be administered directly as a naked nucleic acid construct. Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example lipofectam™ and transfectam™).

Typically, nucleic acid constructs are mixed with the transfection agent to produce a composition. Preferably the naked nucleic acid construct, viral vector comprising the polynucleotide or composition is combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, or transdermal administration.

The pharmaceutical composition is administered in such a way that the polynucleotide of the invention, viral vector for gene therapy, can be incorporated into cells at an appropriate area. When the polynucleotide of the invention is delivered to cells by a viral vector, the amount of virus administered is in the range of from $10^6$ to $10^{10}$ pfu, preferably from $10^7$ to $10^9$ pfu, more preferably about $10^8$ pfu for adenoviral vectors. When injected, typically 1-2 ml of virus in a pharmaceutically acceptable suitable carrier or diluent is administered. When the polynucleotide of the invention is administered as a naked nucleic acid, the amount of nucleic acid administered is typically in the range of from 1 µg to 10 mg.

Where the polynucleotide giving rise to the product is under the control of an inducible promoter, it may only be necessary to induce gene expression for the duration of the treatment. Once the condition has been treated, the inducer is removed and expression of the polypeptide of the invention ceases. This will clearly have clinical advantages. Such a system may, for example, involve administering the antibiotic tetracycline, to activate gene expression via its effect on the tet repressor/VP16 fusion protein.

The use of tissue-specific promoters will be of assistance in the treatment of disease using the polypeptides, polynucleotide and vectors of the invention. It will be advantageous to be able express therapeutic genes in only the relevant affected cell types, especially where such genes are toxic when expressed in other cell types.

The routes of administration and dosages described above are intended only as a guide since a skilled physician will be able to determine readily the optimum route of administration and dosage for any particular patient and condition. The following Example illustrates the invention.

EXAMPLE 1

The target protein BACE1 was amplified by PCR using primers:
AGGAAGTGGAAGTGGCCACCATGGC-CCAAGCCCTGCCC and GTAGGGGTAATTGGC-CTTCAGCAGGGAGATGTCATC.

The PCR product was cloned into an expression vector such that an 8 residue histidine tag was inserted in frame at the C-terminus. This construct was transfected into HEK293 cells that were expanded under conditions selecting for the expression construct.

In a representative experiment BACE was affinity purified from 65 mg of the membrane-enriched fraction derived from approximately $10^8$ transfected cells. Membrane proteins, solubilized in 1% CHAPSO, were incubated with 500 µl Ni—NTA resin and eluted with 150 mM imidazole. The resulting eluate was precleared with sepharose (Pierce) for 1 hour. After discarding the sepharose, the eluate was incubated with anti-His antibody (Serotec) covalently bound to sepharose (Pierce aminolink plus) at 4° C. overnight. Finally immunoprecipitated proteins were resuspended in sample buffer, separated on a 4-12% bis-tris gel under reduced conditions and stained with colloidal Coomassie blue. Bands specific to the tagged cell line were excised and in-gel digested with trypsin. All trypsin digested peptides were subjected to LC/MS/MS and proteins were identified by searching a non-redundant protein database.

Proteins identified in a representative experiment are summarised below.

NogoB (ASY) peptides identified:

```
  1 MEDLDQSPLV SSSDSPPRPQ PAFKYQFVRE PEDEEEEEEE EEEDEDEDLE

51 ELEVLERKPA AGLSAAPVPT APAAGAPLMD FGNDFVPPAP RGPLPAAPPV

101 APERQPCWDP SPVSSTVPAP SPLSAAAVSP SKLPQDDEPP ARPPPPPPAS

151 VSPQAEPVWT PPAPAPAAPP STPAAPKRRG SSGSVVVDLL YWRDIKKTGV

201 VFGASLFLLL SLTVFSIVSV TAYIALALLS VTISFRIYKG VIQAIQKSDE

251 GHPFRAYLES EVAISEELVQ KYSNSALGHV NCTIKELRRL FLVDDLVDSL

301 KFAVLMWVFT YVGALFNGLT LLILALISLF SVPVIYERHQ AQIDHYLGLA

351 NKNVKDAMAK IQAKIPGLKR KAE
```

The underlined peptide is sufficient to distinguish NogoB from other Nogo isoforms.

EXAMPLE 2

Differentiating PC12 Cells and Measuring Neurite Outgrowth

PC12 cells are plated at 1×10$^5$ cells per well in 1.5 ml complete DMEM using a 6-well plate. Plated cells are incubated overnight at 37° C. in 5% $CO_2$ to allow them to attach. Cells are washed with complete, prewarmed DMEM. 1.5 ml low serum DMEM±NGF±Bace±Nogo±test agent is added. A range of concentrations of Bace, Nogo and NGF of 0, 0.1, 1, 10, 50 and 100 ng/ml are tested. The test agent is added to different wells at concentrations of 0, 0.001, 0.01, 0.1, 1 and 10 nM. The cells are then incubated for 48 hours at 37° C. in 5% $CO_2$ to allow them to attach.

After 48 Hours the cells should be about 50% confluent and are fixed in 4% paraformaldehyde phosphate for measurement of neurite outgrowth. Acid fucin stain is diluted (2×) in PBS, mixed and filter sterilised through a syringe. 500 µl of diluted stain is added to each well. Cells are incubated in the stain for 2 minutes at room temperature and washed in PBS (1 ml) four times. Fuchin stains cell bodies and neurites red. Neurite number and length/cell body are measured on an inverted microscope using appropriate image analysis and software.

EXAMPLE 3

Sections from adult transgenic mice (designated Tas10) overexpressing human APP constructs containing the Swedish mutation were stained with a variety of antibody markers. These were chosen to allow the detection of amyloid plaques and proteins associated with or around them.

In a representative experiment a monoclonal antibody against the Nogo-A protein (clone 6D5) was found to stain the sections (for example Tas10 animal 4) in a pattern reminiscent of a ring surrounding most if not all plaque like structures (FIG. 1A).

Figure 1B:
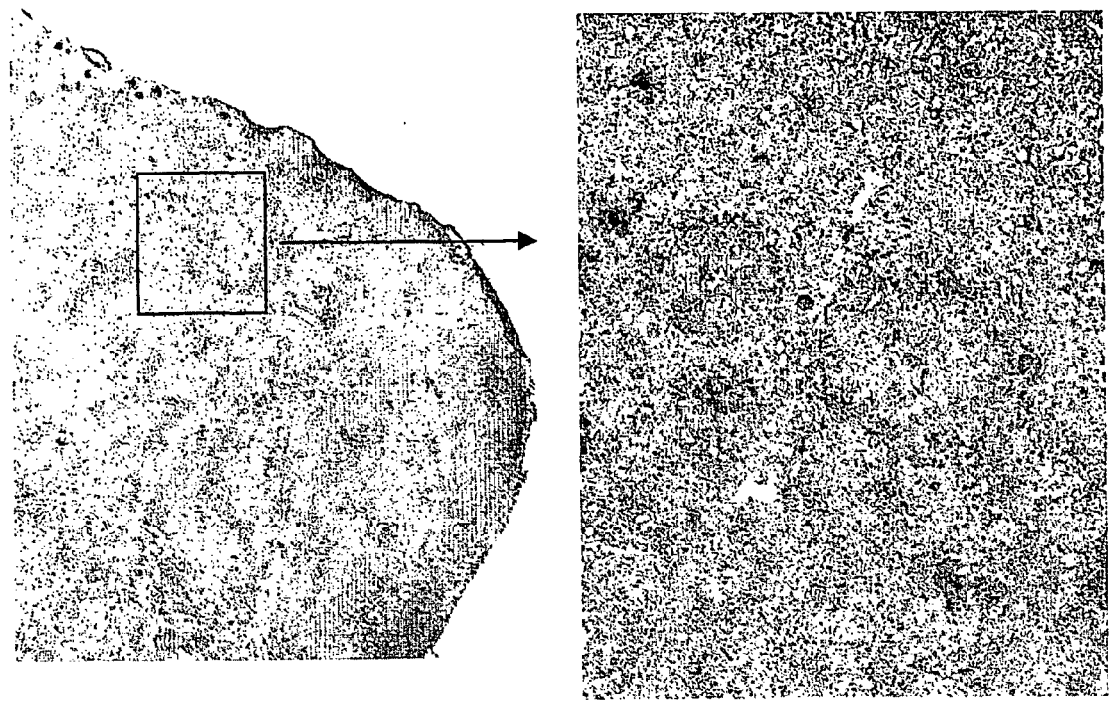
FIG. 1B Left panels show sections stained with an Anti-Nogo-A polyclonal antibody at two different magnifications. The two panels on the right show double staining using the same Nogo-A polyclonal and an anti-Abeta monoclonal 1E8.
Figure 1B:
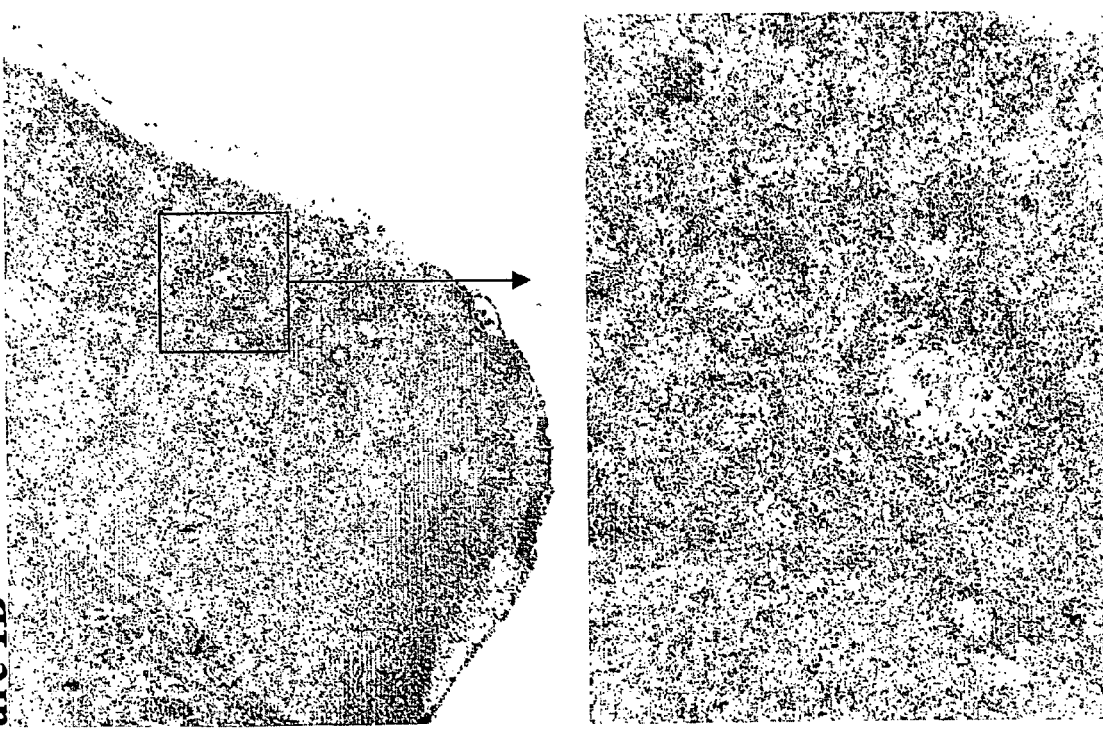

In order to confirm that this was actually plaque associated staining, further sections were double-stained with a monoclonal antibody (clone 1E8) directed against the amyloid peptide together with an affinity purified polyclonal antibody directed against Nogo-A (Alpha Diagnostics). In these sections an intense pink coloured product was deposited in the plaques labelling amyloid protein and these were surrounded by a darker blue/purple product corresponding to sites of Nogo-A protein expression. These observations confirmed our earlier finding of overexpression of Nogo-A around the edges of plaques in regions of new amyloid deposition (FIG. 1B).

Figure 1C:
FIG. 1C Similar ring-like staining with Asp2/BACE specific monoclonal antibody (9B21) in these Tas10 transgenic mice.
Figure 1D:
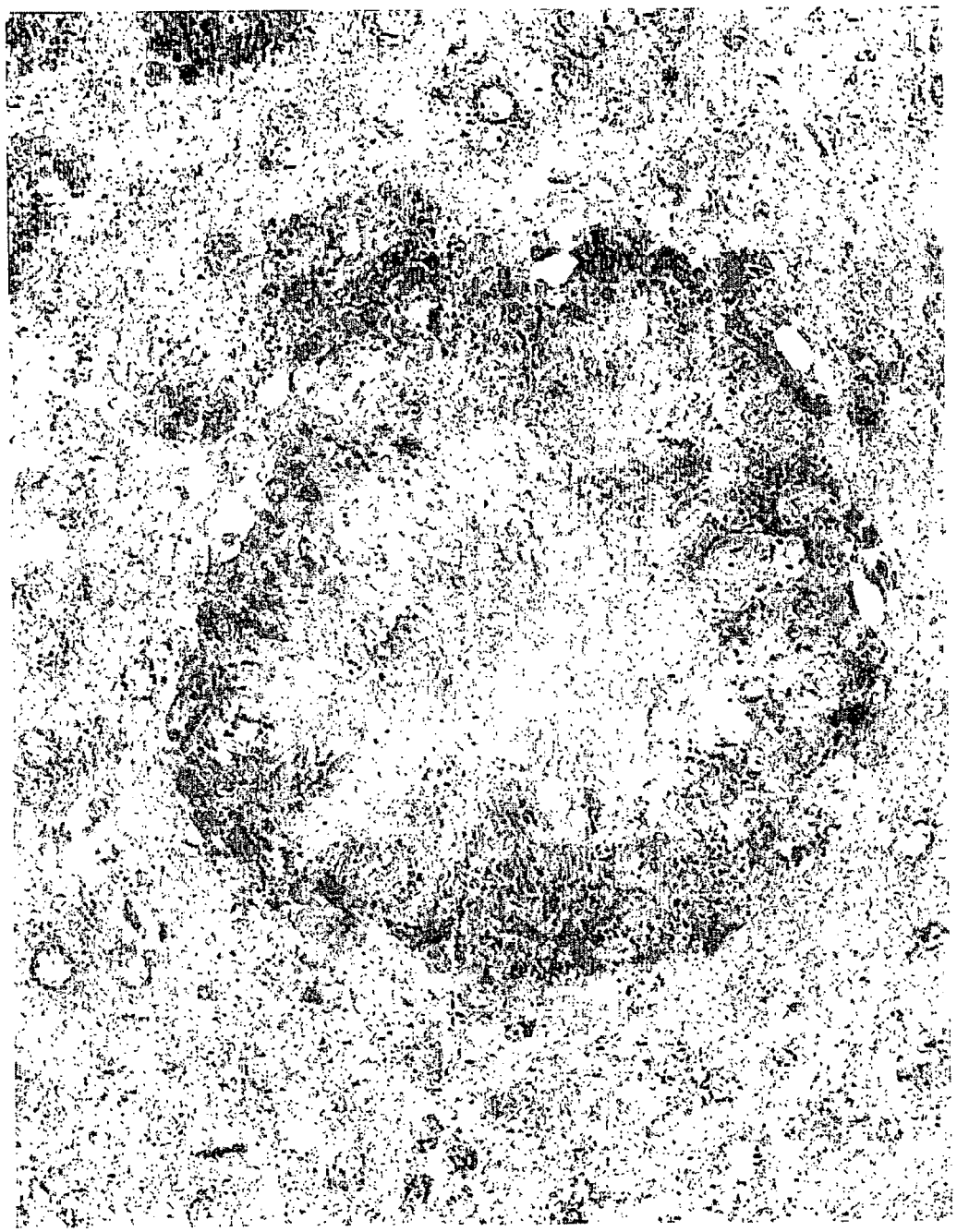
FIG. 1D Asp2/BACE staining of Tas10 transgenic mouse brain sections with monoclonal 9B21 shows a distinctive cellular staining extending in processes into the amyloid plaque core.
Figure 1E:
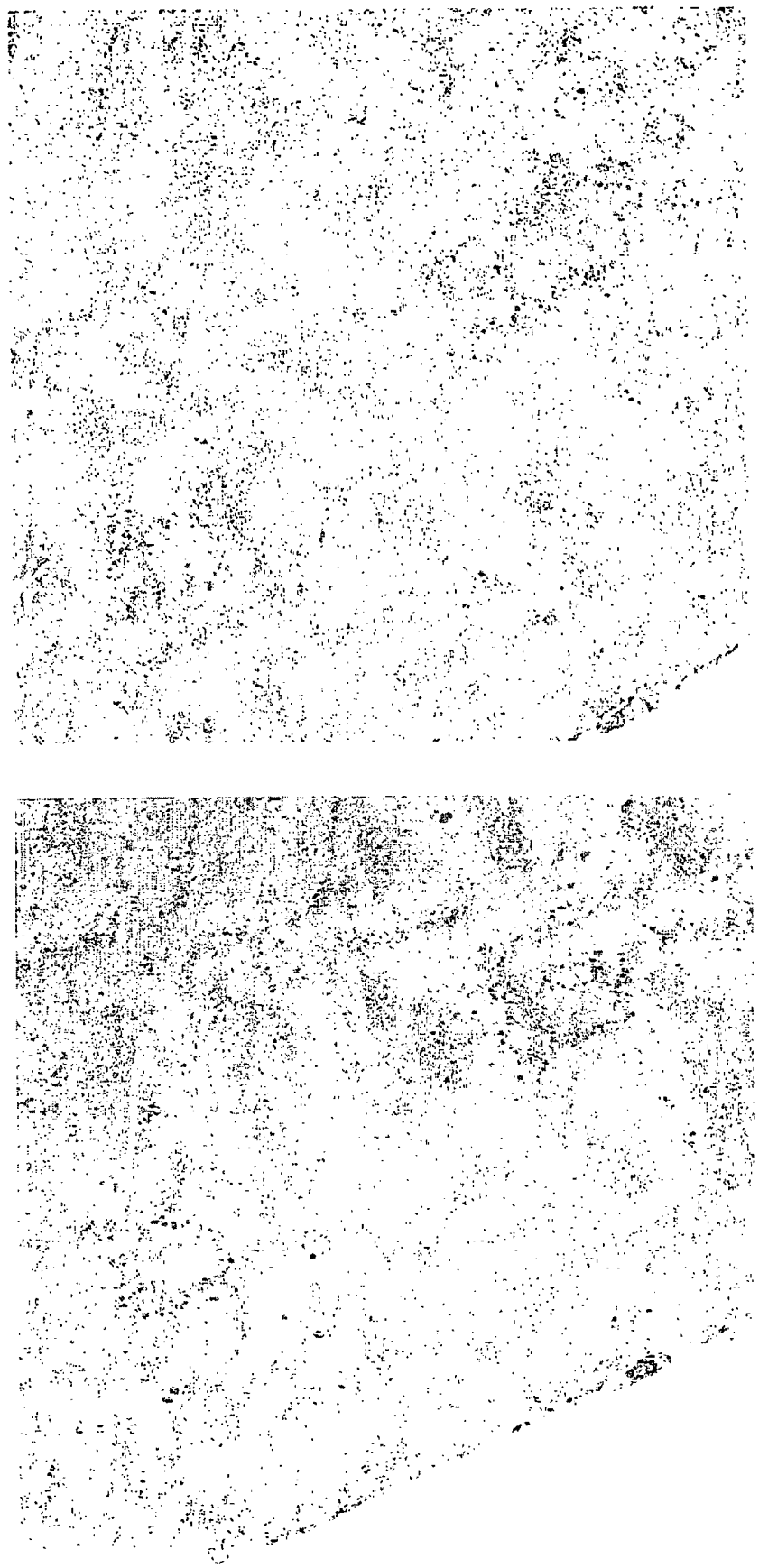
FIG. 1E Sequential sections from mouse #3 (18 month old Tas10 transgenic) stained for Nogo-A (left panel) and Asp2/BACE (right panel). Note the lower levels of Nogo-A overexpression in animals with a lower amyloid load (compared with animal 4 in previous sections). Both proteins show a similar overlapping distribution in all plaques present in both sections.

A number of additional antibody markers including neurofilament (Chemicon), GFAP (Sigma) and phospho-tau (clone AT8) all failed to produce a pattern similar to that seen with the Nogo-A antibodies. A monoclonal antibody directed against Asp2/BACE (clone 9B21) was used to stain sections from the same animal and were found to produce a ring like staining pattern most closely resembling the Nogo-A staining (FIG. 1C). In subsequent serial sections and double-staining experiments it was apparent that the Nogo-A and Asp2/BACE proteins show a remarkably close association (FIG. 1E). The only distinction that could be observed was that the Nogo-A stain was more diffusely distributed than the Asp2/BACE staining which appeared to label discrete cellular structures with features characteristic of neurons in this region (FIG. 1D).

Further confirmation of the correlation of elevated Nogo-A expression with progressive pathology was found in the staining pattern of sections from transgenic animals displaying a lower plaque load. In these sections fewer and smaller plaques were seen and these were surrounded by less intense Nogo-A staining (FIG. 1E).

EXAMPLE 4

To determine the source of the Nogo-A found in the deposits surrounding the plaques cultured neurons that are known to be sensitive to amyloid peptide induced toxicity (in this case embryonic hippocampal neurons) were studied. Similar results can be obtained with other types of cultured neurons.

Figure 2:
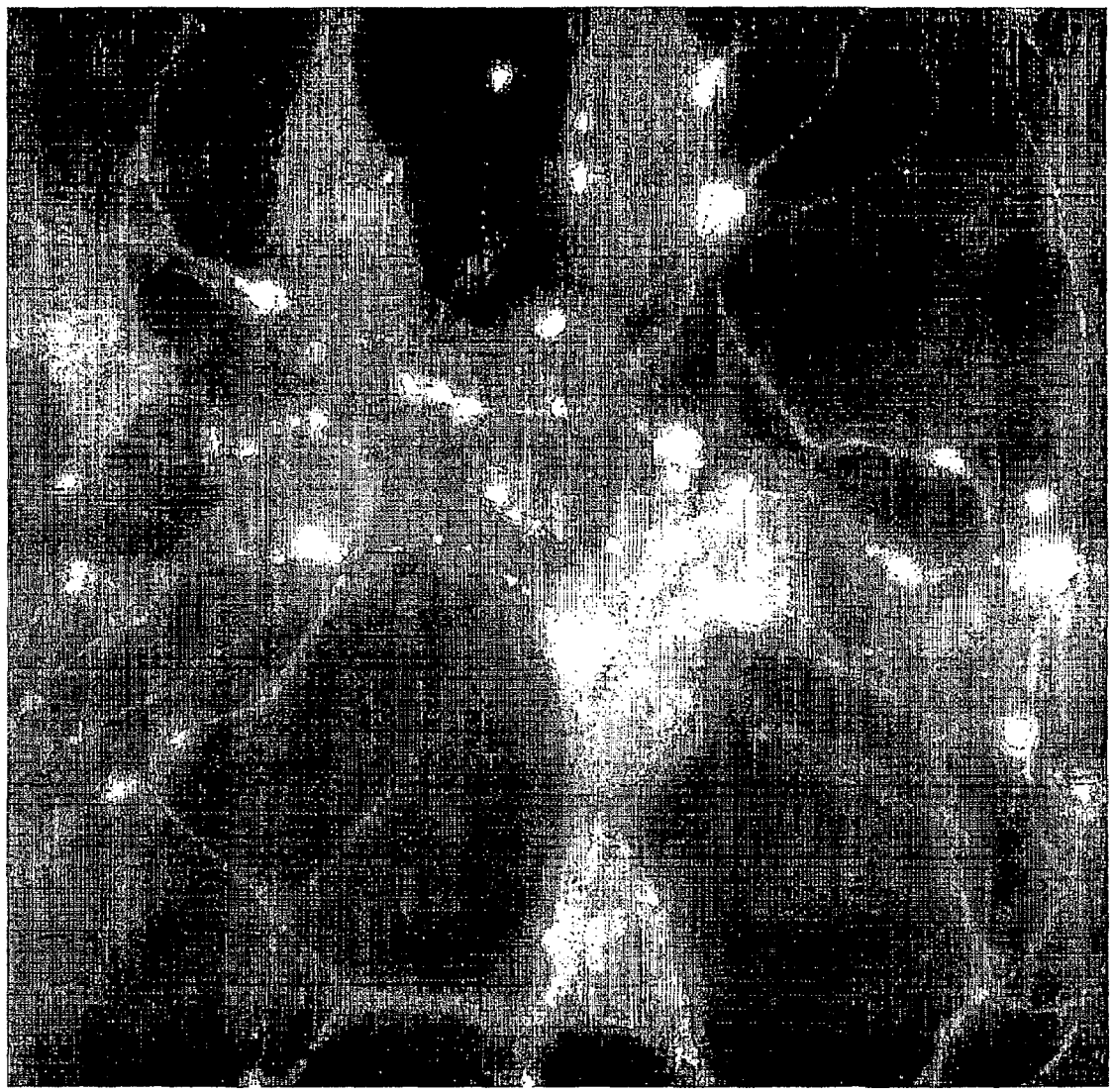
FIG. 2 Embryonic hippocampal neurons express Nogo-A throughout the cytoplasm, with some apparent surface localisation. Concentrations of Nogo-A immunoreactivity are seen in varicosities or synaptic structures along the processes.

Cultured hippocampal neurons were fixed and stained with a Nogo-A specific monoclonal; the cells displayed prominent cytoplasmic and axonal staining with some apparent cell surface clusters. In relatively mature cultures the Nogo-A can be seen to also show some concentration in varicosities along the processes that may represent synapses (FIG. 2). Treatment of such cultures with Abeta1-42 peptide can be used to determine their effects on Nogo-A expression and further used as a system to identify molecules that alter those responses as a means of modifying the progression and pathology of diseases such as (but not limited to) Alzheimer's disease.

EXAMPLE 5

Figure 3A:
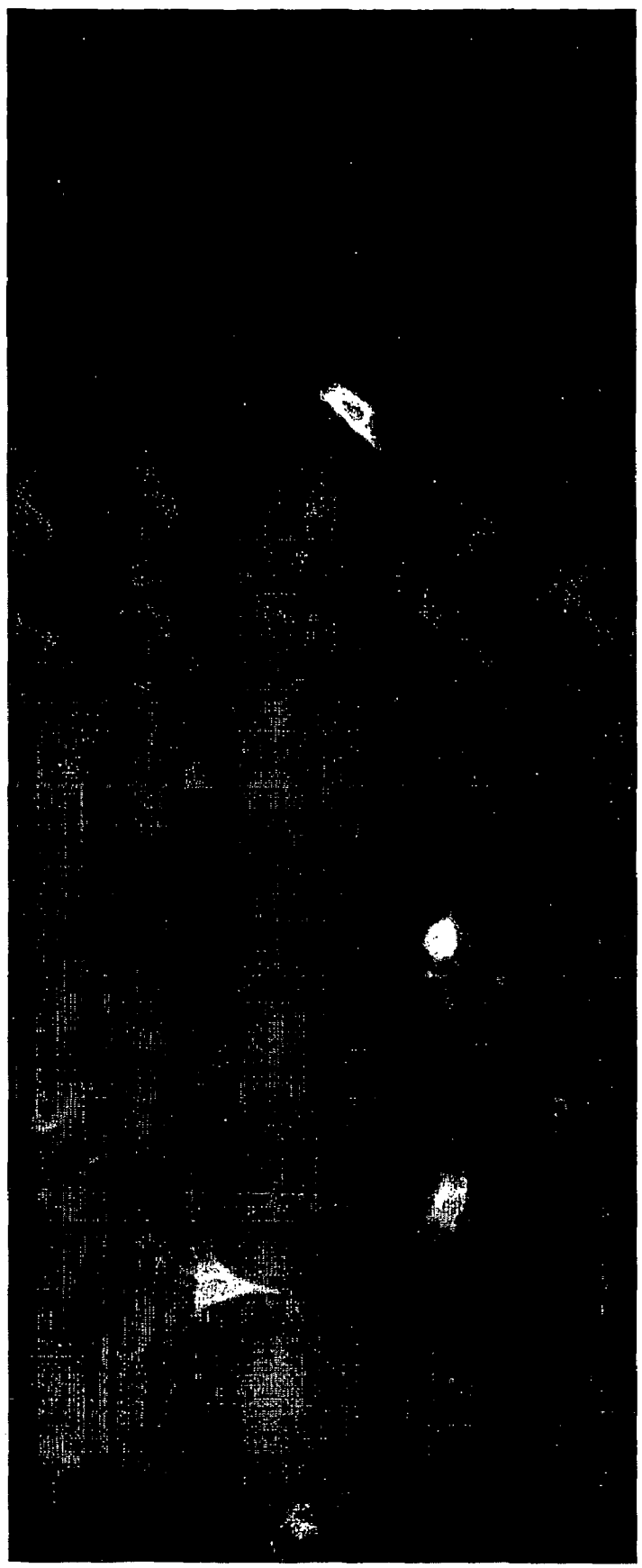
FIG. 3A Transient transfections produce high levels of Asp2/BACE and Nogo-A protein in SHSY5Y-APPswe cells. The left panel shows cells transfected with Asp2/BACE and stained with Anti-myc tag clone 9E10. The right panel shows cells transfected with Nogo-A and stained with a specific monoclonal antibody (clone 6D5).

Human neuroblastoma cells (SHSY5Y) stably over-expressing the human APP gene carrying the Swedish mutation which predisposes affected individuals to early onset Alzheimer's disease can provide a useful system in which to study the effects of modifying agents on processing of APP into toxic Abeta peptide fragments. These cells normally secrete readily detectable levels of Abeta peptide into the culture medium. Transfection of Nogo-A, Nogo-B or Nogo-C alone or in combination with BACE/Asp2 can be used to determine the effects of overexpression of these proteins on APP. Repression of Abeta formation by Nogo isoforms would be likely to indicate that the overexpression of Nogo-A seen around the plaques in the Tas10 mice represents a compensatory/protective mechanism while an increase would suggest that elevated expression contributes to the pathology of Alzheimer's disease in particular and neurodegenerative diseases in general. Screens of molecules altering the interactions of Nogo with BACE/Asp2 could thus be configured to identify agonists or antagonists of the binding as required.

cDNAs encoding Nogo isoforms were transfected into cultured SHSY5Y-APPswe cells and expressed proteins detected in fixed cells with immunohistochemistry. Asp2 was detected using a c-terminal myc epitope (FIG. 3A left panel) while the Nogo-A (FIG. 3A right panel) and B isoforms were detected using isoform specific rabbit polyclonal antibodies (designated 67 and 66 respectively or monoclonal Anti-Nogo-A 6D5 as indicated in the figure legends). These experiments confirm that it is possible to overexpress these proteins in this cellular background and can be used as the basis of an assay for modulators of Nogo influenced APP processing.

Figure 3B:
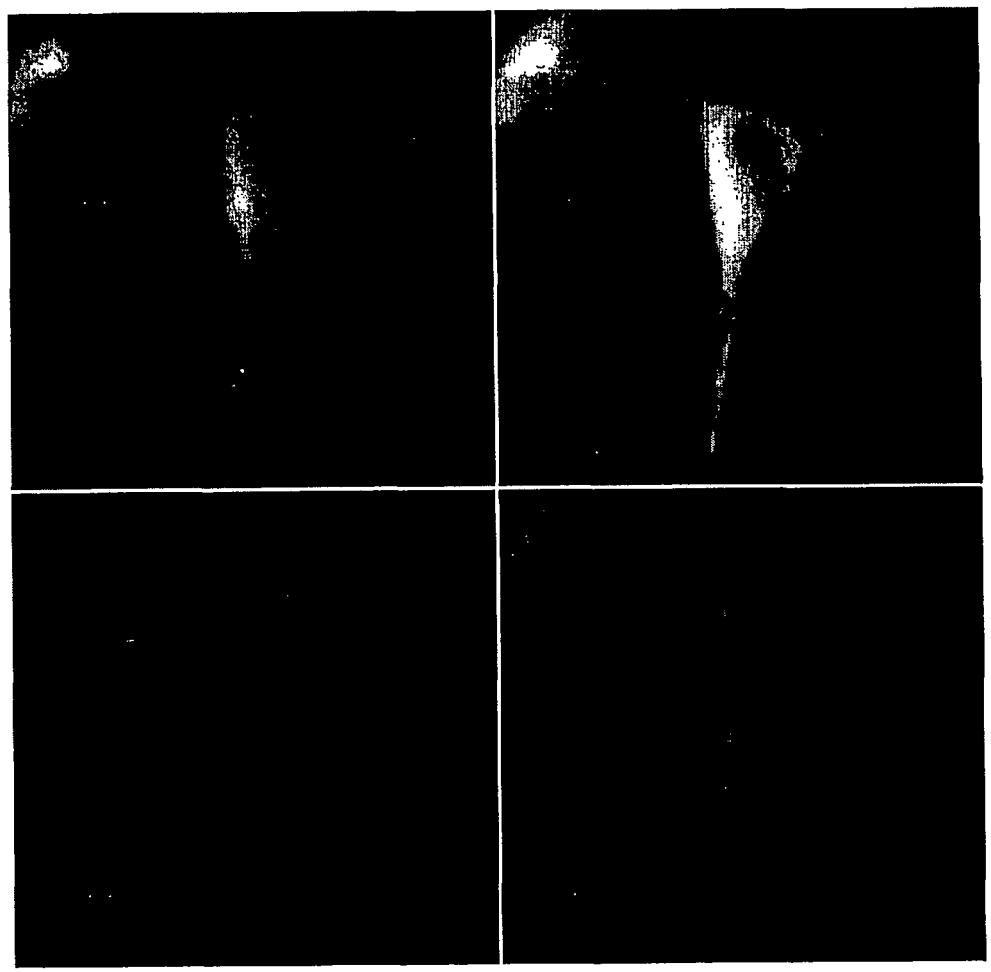
FIG. 3B Cotransfection of Asp2/BACE-myc and Nogo-A into SHSY5Y cells. Panels showing the following stains. Top left Hoescht nuclear stain; Top right Asp2/BACE-myc; Bottom left Nogo-A polyclonal 67; Bottom right Merge of Asp2/BACE and Nogo-A stains. Note codistribution of a pool of Asp2/BACE with Nogo-A in the double-transfected cells.
Figure 3C:
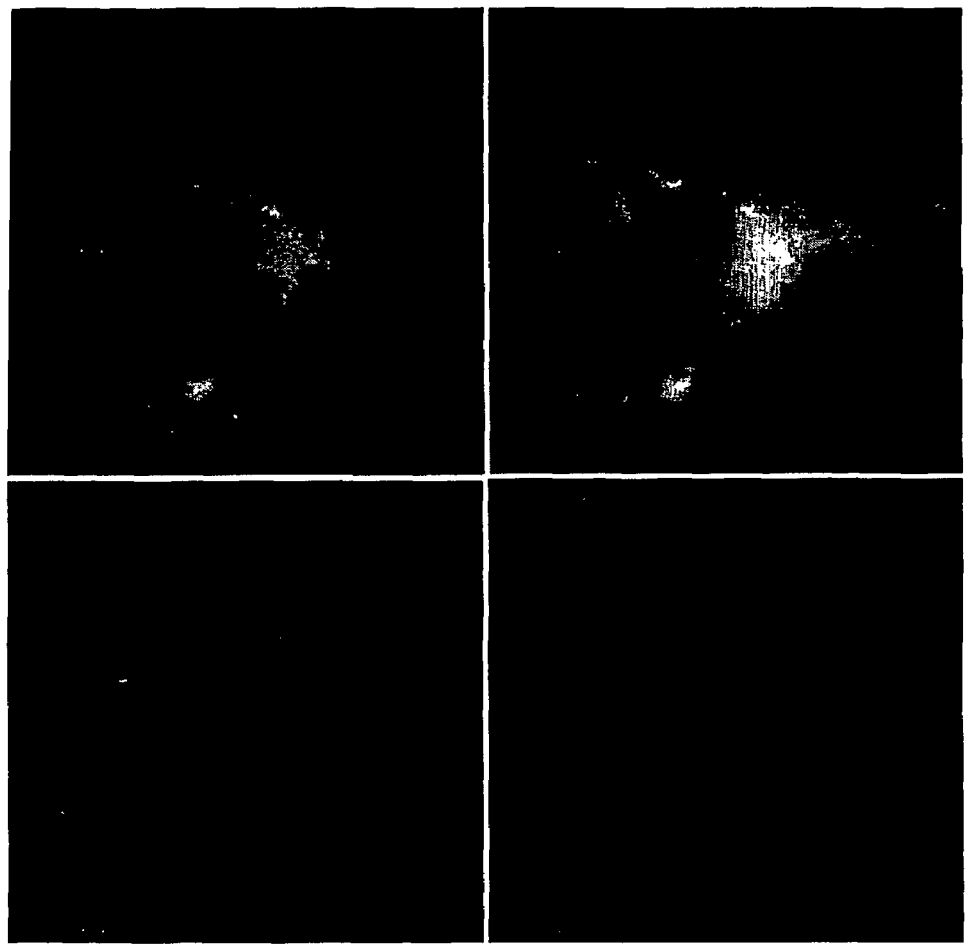
FIG. 3C Cotransfection of Asp2/BACE-myc and Nogo-B into SHSY5Y cells. Panels showing the following stains. Top left Hoescht nuclear stain; Top right Asp2/BACE-myc; Bottom left Nogo-B polyclonal 66; Bottom right Merge of Asp2/BACE and Nogo-B stains. Note codistribution of a pool of Asp2/BACE with Nogo-B in the double-transfected cells.

Furthermore, in double transfected cells, microscopic examination was able to demonstrate the co-localisation of some of the transfected proteins within the cells. These data suggest that both Nogo-A (FIG. 3A) and Nogo-B (FIG. 3B) show the ability to interact with Asp2/BACE in an appropriate cellular background and that this interaction may well be responsible for altering the processing of APP during plaque formation.

EXAMPLE 6

Figure 4A:
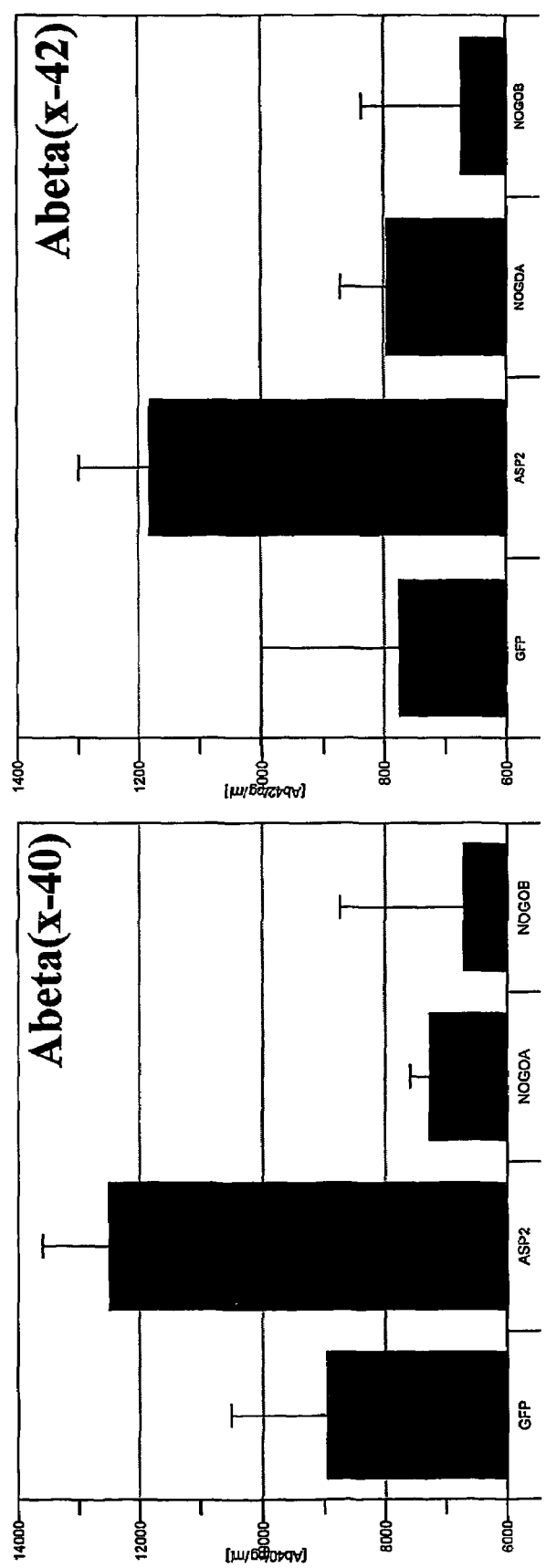
FIG. 4A Nogo Isoform overexpression does not enhance Abeta production in SHSH5Y-APPswe cells. Left panel shows effects of transfections into SHSY5Y-APPswedish cells on Abeta X-40 production. The right panel shows the effects of transfections on AbetaX-42 production. Bars represent the activity after transfection with GFP, Asp2/BACE, Nogo-A and Nogo-B respectively in each panel. Note Asp2/BACE increases Abeta production in these cells at this cell density while single transfection of the two Nogo isoforms appears not to enhance production at this cell density.

The human neuroblastoma cell-line SHSY5Y-APPswedish can be transfected with cDNAs encoding test constructs and the effects on APP processing and secretion of Abeta into the media can be measured using ELISA assays. In experiments performed at low cell-densities we were able to detect an enhanced production of Abeta x-40 and x-42 following transfection of an Asp2/BACE construct (FIG. 4A). Cells transfected with Nogo-A or Nogo-B expressing constructs in parallel were found not to produce the same increase in Abeta production suggesting they are not sufficient alone for enhanced amyloidogenesis.

Figure 4B:
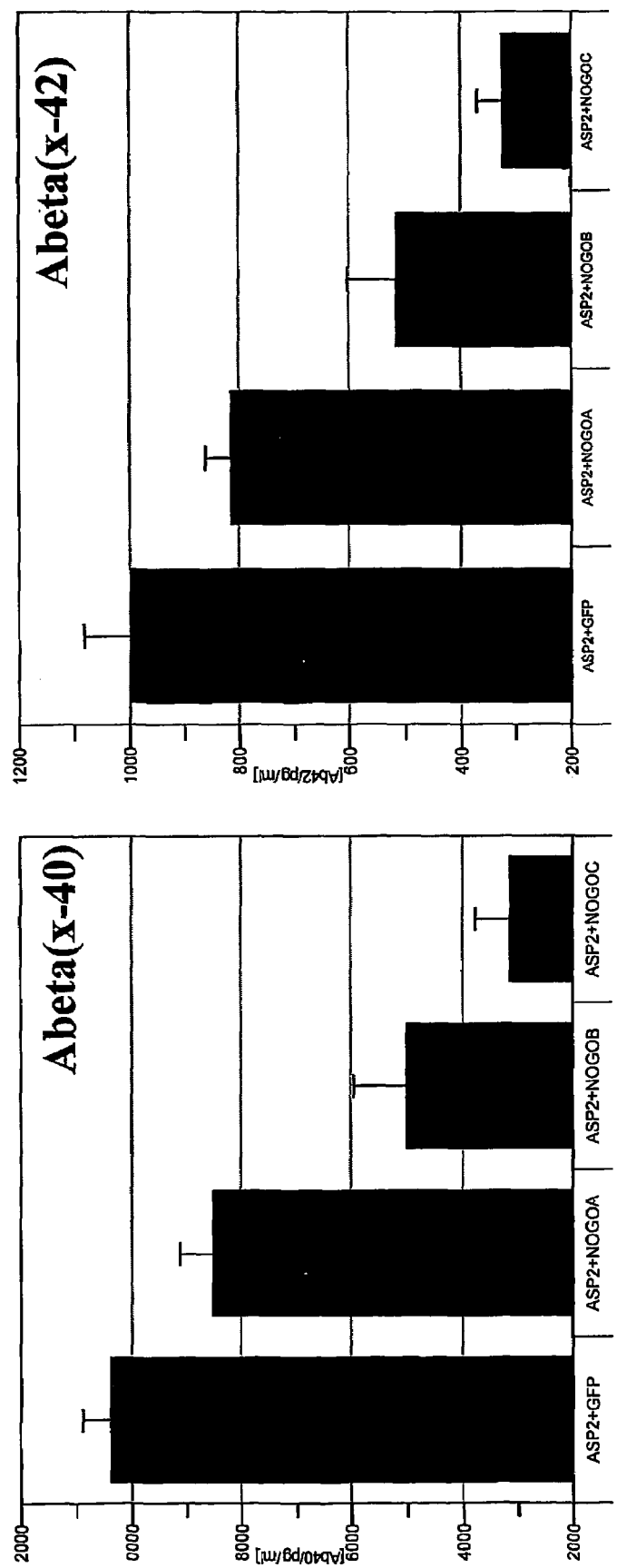
FIG. 4B. Co-expression of Nogo isoforms with Asp2/BACE modulates Ab production in SHSY5Y-APPswe cells. Assays measuring AbetaX-40 (left panel) and AbetaX-42 (right panel) were conducted on cells cotransfected with the indicated combinations of DNA in the following order. Asp2/BACE plus GFP; Asp2/BACE plus Nogo-A; Asp2/BACE plus Nogo-B; Asp2/BACE plus Nogo-C. Double transfections can be used to assay the activity of Nogo isoforms on APP processing.

In further experiments the effects of co-expression of all three Nogo isoforms with Asp2/BACE was tested. Analysis of conditioned media suggests that the Nogo isoforms appear to significantly reduce the levels of detectable Abeta peptide (FIG. 4B). The observed alterations in Abeta levels may be due to the direct intracellular interaction of Asp2/BACE with Nogo which was found by co-immunoprecipitation of these proteins from cell lysates. This is supported by their co-localisation in transfected cells and therefore the modulation may be at the level of sub-cellular localisation. Since all the Nogo isoforms have a C-terminal ER retention motif the observed changes in Asp2/BACE activity with increased Nogo expression could cause the retention of more Asp2/BACE within the endoplasmic reticulum awayfrom the sites of normal APP processing.

The invention claimed is:

1. A method of identifying a modulator of Nogo function, the method comprising:
(i) providing:
  (a) a BACE polypeptide having SEQ ID NO:2;
  (b) a Nogo polypeptide having a sequence selected from SEQ ID NOs:4-7, SEQ ID NO:9, SEQ ID NO:11;
  (c) a test agent
under conditions that would permit binding of said BACE polypeptide to said Nogo polypeptide in the absence of said test agent;
(ii) monitoring Nogo mediated activity; and
(iii) wherein a change in BACE mediated activity in the presence of said test agent, compared to BACE mediated activity in the absence of said test agent, indicates said test agent is a modulator of Nogo activity.

2. A method according to claim 1 wherein step (ii) comprises monitoring the binding of said BACE polypeptide to said Nogo polypeptide.

3. A method according to claim 2 wherein said test agent inhibits the binding of said BACE polypeptide to said Nogo polypeptide.

4. A method according to claim 2 wherein said test agent enhances the binding of said BACE polypeptide to said Nogo polypeptide.

5. A method according to claim 1 wherein step (ii) comprises monitoring protease activity.

6. A method according to claim 5 wherein said protease activity is B-secretase cleavage of amyloid precursor protein.

7. A method according to claim 5 wherein said test agent inhibits said protease activity.

8. A method according to claim 1 wherein said Nogo polypeptide is selected from NogoB (SEQ ID NO:4) and fragments of NogoB capable of binding BACE.

* * * * *

UNITED STATES PATENT AND TRADEMARK OFFICE
CERTIFICATE OF CORRECTION

| | | |
|---|---|---|
| PATENT NO. | : 7,270,962 B2 | Page 1 of 1 |
| APPLICATION NO. | : 10/466258 | |
| DATED | : September 18, 2007 | |
| INVENTOR(S) | : Walter Philip Blackstock et al. | |

It is certified that error appears in the above-identified patent and that said Letters Patent is hereby corrected as shown below:

On Title page item (30) Foreign Application Priority Data should read
--Jan. 18, 2001 (GB) 0101312.7--

Signed and Sealed this

Twenty-seventh Day of November, 2007

JON W. DUDAS
*Director of the United States Patent and Trademark Office*

UNITED STATES PATENT AND TRADEMARK OFFICE
CERTIFICATE OF CORRECTION

PATENT NO. : 7,270,962 B2  Page 1 of 1
APPLICATION NO. : 10/466258
DATED : September 18, 2007
INVENTOR(S) : Walter Philip Blackstock et al.

It is certified that error appears in the above-identified patent and that said Letters Patent is hereby corrected as shown below:

On Title page item (30) Foreign Application Priority Data should read --Jan. 18, 2001 (GB) 0101312.7--

Signed and Sealed this

Eighteenth Day of December, 2007

JON W. DUDAS
*Director of the United States Patent and Trademark Office*

SEQUENCE LISTING

<160> NUMBER OF SEQ ID NOS: 13

<210> SEQ ID NO 1
<211> LENGTH: 2526
<212> TYPE: DNA
<213> ORGANISM: Homo sapiens
<220> FEATURE:
<221> NAME/KEY: CDS
<222> LOCATION: (454)..(1959)

<400> SEQUENCE: 1

```
ccacgcgtcc gcagcccgcc cgggagctgc gagccgcgag ctggattatg gtggcctgag      60
cagccaacgc agccgcagga gcccggagcc cttgcccctg cccgcgccgc cgcccgccgg     120
ggggaccagg gaagccgcca ccggcccgcc atgcccgccc ctcccagccc cgccgggagc     180
ccgcgcccgc tgcccaggct ggccgccgcc gtgccgatgt agcgggctcc ggatcccagc     240
ctctcccctg ctcccgtgct ctgcggatct ccctgaccg ctctccacag cccggacccg      300
ggggctggcc cagggccctg caggccctgg cgtcctgatg cccccaagct ccctctcctg     360
agaagccacc agcaccaccc agacttgggg gcaggcgcca gggacggacg tgggccagtg     420
cgagcccaga gggcccgaag ccgggggccc acc atg gcc caa gcc ctg ccc tgg      474
                                    Met Ala Gln Ala Leu Pro Trp
                                     1               5 ctc ctg ctg tgg atg ggc gcg gga gtg ctg cct gcc cac ggc acc cag      522
Leu Leu Leu Trp Met Gly Ala Gly Val Leu Pro Ala His Gly Thr Gln
         10                  15                  20 cac ggc atc cgg ctg ccc ctg cgc agc ggc ctg ggg ggc gcc ccc ctg      570
His Gly Ile Arg Leu Pro Leu Arg Ser Gly Leu Gly Gly Ala Pro Leu
     25                  30                  35 ggg ctg cgg ctg ccc cgg gag acc gac gaa gag ccc gag gag ccc ggc      618
Gly Leu Arg Leu Pro Arg Glu Thr Asp Glu Glu Pro Glu Glu Pro Gly
 40                  45                  50                  55 cgg agg ggc agc ttt gtg gag atg gtg gac aac ctg agg ggc aag tcg      666
Arg Arg Gly Ser Phe Val Glu Met Val Asp Asn Leu Arg Gly Lys Ser
                 60                  65                  70 ggg cag ggc tac tac gtg gag atg acc gtg ggc agc ccc ccg cag acg      714
Gly Gln Gly Tyr Tyr Val Glu Met Thr Val Gly Ser Pro Pro Gln Thr
             75                  80                  85 ctc aac atc ctg gtg gat aca ggc agc agt aac ttt gca gtg ggt gct      762
Leu Asn Ile Leu Val Asp Thr Gly Ser Ser Asn Phe Ala Val Gly Ala
         90                  95                 100
```

-continued

| | |
|---|---|
| gcc ccc cac ccc ttc ctg cat cgc tac tac cag agg cag ctg tcc agc<br>Ala Pro His Pro Phe Leu His Arg Tyr Tyr Gln Arg Gln Leu Ser Ser<br>105                     110                     115 | 810 |
| aca tac cgg gac ctc cgg aag ggt gtg tat gtg ccc tac acc cag ggc<br>Thr Tyr Arg Asp Leu Arg Lys Gly Val Tyr Val Pro Tyr Thr Gln Gly<br>120                   125                   130                   135 | 858 |
| aag tgg gaa ggg gag ctg ggc acc gac ctg gta agc atc ccc cat ggc<br>Lys Trp Glu Gly Glu Leu Gly Thr Asp Leu Val Ser Ile Pro His Gly<br>                   140                   145                   150 | 906 |
| ccc aac gtc act gtg cgt gcc aac att gct gcc atc act gaa tca gac<br>Pro Asn Val Thr Val Arg Ala Asn Ile Ala Ala Ile Thr Glu Ser Asp<br>155                     160                   165 | 954 |
| aag ttc ttc atc aac ggc tcc aac tgg gaa ggc atc ctg ggg ctg gcc<br>Lys Phe Phe Ile Asn Gly Ser Asn Trp Glu Gly Ile Leu Gly Leu Ala<br>       170                   175                   180 | 1002 |
| tat gct gag att gcc agg cct gac gac tcc ctg gag cct ttc ttt gac<br>Tyr Ala Glu Ile Ala Arg Pro Asp Asp Ser Leu Glu Pro Phe Phe Asp<br>185                     190                   195 | 1050 |
| tct ctg gta aag cag acc cac gtt ccc aac ctc ttc tcc ctg cag ctt<br>Ser Leu Val Lys Gln Thr His Val Pro Asn Leu Phe Ser Leu Gln Leu<br>200                     205                   210                   215 | 1098 |
| tgt ggt gct ggc ttc ccc ctc aac cag tct gaa gtg ctg gcc tct gtc<br>Cys Gly Ala Gly Phe Pro Leu Asn Gln Ser Glu Val Leu Ala Ser Val<br>                   220                   225                   230 | 1146 |
| gga ggg agc atg atc att gga ggt atc gac cac tcg ctg tac aca ggc<br>Gly Gly Ser Met Ile Ile Gly Gly Ile Asp His Ser Leu Tyr Thr Gly<br>                   235                   240                   245 | 1194 |
| agt ctc tgg tat aca ccc atc cgg cgg gag tgg tat tat gag gtg atc<br>Ser Leu Trp Tyr Thr Pro Ile Arg Arg Glu Trp Tyr Tyr Glu Val Ile<br>250                     255                   260 | 1242 |
| att gtg cgg gtg gag atc aat gga cag gat ctg aaa atg gac tgc aag<br>Ile Val Arg Val Glu Ile Asn Gly Gln Asp Leu Lys Met Asp Cys Lys<br>265                     270                   275 | 1290 |
| gag tac aac tat gac aag agc att gtg gac agt ggc acc acc aac ctt<br>Glu Tyr Asn Tyr Asp Lys Ser Ile Val Asp Ser Gly Thr Thr Asn Leu<br>280                     285                   290                   295 | 1338 |
| cgt ttg ccc aag aaa gtg ttt gaa gct gca gtc aaa tcc atc aag gca<br>Arg Leu Pro Lys Lys Val Phe Glu Ala Ala Val Lys Ser Ile Lys Ala<br>                   300                   305                   310 | 1386 |
| gcc tcc tcc acg gag aag ttc cct gat ggt ttc tgg cta gga gag cag<br>Ala Ser Ser Thr Glu Lys Phe Pro Asp Gly Phe Trp Leu Gly Glu Gln<br>                   315                   320                   325 | 1434 |
| ctg gtg tgc tgg caa gca ggc acc acc cct tgg aac att ttc cca gtc<br>Leu Val Cys Trp Gln Ala Gly Thr Thr Pro Trp Asn Ile Phe Pro Val<br>330                     335                   340 | 1482 |
| atc tca ctc tac cta atg ggt gag gtt acc aac cag tcc ttc cgc atc<br>Ile Ser Leu Tyr Leu Met Gly Glu Val Thr Asn Gln Ser Phe Arg Ile<br>345                     350                   355 | 1530 |
| acc atc ctt ccg cag caa tac ctg cgg cca gtg gaa gat gtg gcc acg<br>Thr Ile Leu Pro Gln Gln Tyr Leu Arg Pro Val Glu Asp Val Ala Thr<br>360                     365                   370                   375 | 1578 |
| tcc caa gac gac tgt tac aag ttt gcc atc tca cag tca tcc acg ggc<br>Ser Gln Asp Asp Cys Tyr Lys Phe Ala Ile Ser Gln Ser Ser Thr Gly<br>                   380                   385                   390 | 1626 |
| act gtt atg gga gct gtt atc atg gag ggc ttc tac gtt gtc ttt gat<br>Thr Val Met Gly Ala Val Ile Met Glu Gly Phe Tyr Val Val Phe Asp<br>                   395                   400                   405 | 1674 |
| cgg gcc cga aaa cga att ggc ttt gct gtc agc gct tgc cat gtg cac<br>Arg Ala Arg Lys Arg Ile Gly Phe Ala Val Ser Ala Cys His Val His | 1722 |

-continued

```
                            410                 415                 420
gat gag ttc agg acg gca gcg gtg gaa ggc cct ttt gtc acc ttg gac        1770
Asp Glu Phe Arg Thr Ala Ala Val Glu Gly Pro Phe Val Thr Leu Asp
        425                 430                 435 atg gaa gac tgt ggc tac aac att cca cag aca gat gag tca acc ctc        1818
Met Glu Asp Cys Gly Tyr Asn Ile Pro Gln Thr Asp Glu Ser Thr Leu
440                 445                 450                 455 atg acc ata gcc tat gtc atg gct gcc atc tgc gcc ctc ttc atg ctg        1866
Met Thr Ile Ala Tyr Val Met Ala Ala Ile Cys Ala Leu Phe Met Leu
                460                 465                 470 cca ctc tgc ctc atg gtg tgt cag tgg cgc tgc ctc cgc tgc ctg cgc        1914
Pro Leu Cys Leu Met Val Cys Gln Trp Arg Cys Leu Arg Cys Leu Arg
        475                 480                 485 cag cag cat gat gac ttt gct gat gac atc tcc ctg ctg aag tga            1959
Gln Gln His Asp Asp Phe Ala Asp Asp Ile Ser Leu Leu Lys
        490                 495                 500 ggaggcccat gggcagaaga tagagattcc cctggaccac acctccgtgg ttcactttgg      2019
tcacaagtag gagacacaga tggcacctgt ggccagagca cctcaggacc ctccccaccc      2079
accaaatgcc tctgccttga tggagaagga aaaggctggc aagtgggtt ccagggactg       2139 tacctgtagg aaacagaaaa gagaagaaag aagcactctg ctggcgggaa tactcttggt      2199
cacctcaaat ttaagtcggg aaattctgct gcttgaaact tcagccctga acctttgtcc      2259
accattcctt taaattctcc aacccaaagt attcttcttt tcttagtttc agaagtactg      2319
gcatcacacg caggttacct tggcgtgtgt ccctgtggta ccctggcaga aagagacca      2379 agcttgtttc cctgctggcc aaagtcagta ggagaggatg cacagtttgc tatttgcttt     2439
agagacaggg actgtataaa caagcctaac attggtgcaa agattgcctc ttgaattaaa      2499
aaaaaaaact agaaaaaaaa aaaaaaa                                          2526
```

<210> SEQ ID NO 2
<211> LENGTH: 501
<212> TYPE: PRT
<213> ORGANISM: Homo sapiens

<400> SEQUENCE: 2

```
Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160
```

-continued

```
Ala Ala Ile Thr Glu Ser Asp Lys Phe Phe Ile Asn Gly Ser Asn Trp
            165                 170                 175
Glu Gly Ile Leu Gly Leu Ala Tyr Ala Glu Ile Ala Arg Pro Asp Asp
        180                 185                 190
Ser Leu Glu Pro Phe Phe Asp Ser Leu Val Lys Gln Thr His Val Pro
    195                 200                 205
Asn Leu Phe Ser Leu Gln Leu Cys Gly Ala Gly Phe Pro Leu Asn Gln
210                 215                 220
Ser Glu Val Leu Ala Ser Val Gly Gly Ser Met Ile Ile Gly Gly Ile
225                 230                 235                 240
Asp His Ser Leu Tyr Thr Gly Ser Leu Trp Tyr Thr Pro Ile Arg Arg
                245                 250                 255
Glu Trp Tyr Tyr Glu Val Ile Ile Val Arg Val Glu Ile Asn Gly Gln
            260                 265                 270
Asp Leu Lys Met Asp Cys Lys Glu Tyr Asn Tyr Asp Lys Ser Ile Val
        275                 280                 285
Asp Ser Gly Thr Thr Asn Leu Arg Leu Pro Lys Lys Val Phe Glu Ala
    290                 295                 300
Ala Val Lys Ser Ile Lys Ala Ala Ser Ser Thr Glu Lys Phe Pro Asp
305                 310                 315                 320
Gly Phe Trp Leu Gly Glu Gln Leu Val Cys Trp Gln Ala Gly Thr Thr
                325                 330                 335
Pro Trp Asn Ile Phe Pro Val Ile Ser Leu Tyr Leu Met Gly Glu Val
            340                 345                 350
Thr Asn Gln Ser Phe Arg Ile Thr Ile Leu Pro Gln Gln Tyr Leu Arg
        355                 360                 365
Pro Val Glu Asp Val Ala Thr Ser Gln Asp Asp Cys Tyr Lys Phe Ala
    370                 375                 380
Ile Ser Gln Ser Ser Thr Gly Thr Val Met Gly Ala Val Ile Met Glu
385                 390                 395                 400
Gly Phe Tyr Val Val Phe Asp Arg Ala Arg Lys Arg Ile Gly Phe Ala
                405                 410                 415
Val Ser Ala Cys His Val His Asp Glu Phe Arg Thr Ala Ala Val Glu
            420                 425                 430
Gly Pro Phe Val Thr Leu Asp Met Glu Asp Cys Gly Tyr Asn Ile Pro
        435                 440                 445
Gln Thr Asp Glu Ser Thr Leu Met Thr Ile Ala Tyr Val Met Ala Ala
    450                 455                 460
Ile Cys Ala Leu Phe Met Leu Pro Leu Cys Leu Met Val Cys Gln Trp
465                 470                 475                 480
Arg Cys Leu Arg Cys Leu Arg Gln Gln His Asp Asp Phe Ala Asp Asp
                485                 490                 495
Ile Ser Leu Leu Lys
            500

<210> SEQ ID NO 3
<211> LENGTH: 2052
<212> TYPE: DNA
<213> ORGANISM: Homo sapiens
<220> FEATURE:
<221> NAME/KEY: CDS
<222> LOCATION: (67)..(1188)

<400> SEQUENCE: 3
cgcggctctg agacgcggcc ccggcggcgg cggcagcagc tgcagcatca tctccaccct    60
```

```
ccagcc atg gaa gac ctg gac cag tct cct ctg gtc tcg tcc tcg gac      108
       Met Glu Asp Leu Asp Gln Ser Pro Leu Val Ser Ser Ser Asp
        1               5                  10 agc cca ccc cgg ccg cag ccc gcg ttc aag tac cag ttc gtg agg gag      156
Ser Pro Pro Arg Pro Gln Pro Ala Phe Lys Tyr Gln Phe Val Arg Glu
 15              20                  25                  30 ccc gag gac gag gag gaa gaa gag gag gag gaa gag gag gac gag gac      204
Pro Glu Asp Glu Glu Glu Glu Glu Glu Glu Glu Glu Glu Asp Glu Asp
                 35                  40                  45 gaa gac ctg gag gag ctg gag gtg ctg gag agg aag ccc gcc gcc ggg      252
Glu Asp Leu Glu Glu Leu Glu Val Leu Glu Arg Lys Pro Ala Ala Gly
             50                  55                  60 ctg tcc gcg gcc cca gtg ccc acc gcc cct gcc gcc ggc gcg ccc ctg      300
Leu Ser Ala Ala Pro Val Pro Thr Ala Pro Ala Ala Gly Ala Pro Leu
         65                  70                  75 atg gac ttc gga aat gac ttc gtg ccg ccg gcg ccc cgg gga ccc ctg      348
Met Asp Phe Gly Asn Asp Phe Val Pro Pro Ala Pro Arg Gly Pro Leu
     80                  85                  90 ccg gcc gct ccc ccc gtc gcc ccg gag cgg cag ccg tgt tgg gac ccg      396
Pro Ala Ala Pro Pro Val Ala Pro Glu Arg Gln Pro Cys Trp Asp Pro
 95              100                 105                 110 agc ccg gtg tcg tcg acc gtg ccc gcg cca tcc ccg ctg tct gct gcc      444
Ser Pro Val Ser Ser Thr Val Pro Ala Pro Ser Pro Leu Ser Ala Ala
                115                 120                 125 gca gtc tcg ccc tcc aag ctc cct cag gac gac gag cct ccg gcc cgg      492
Ala Val Ser Pro Ser Lys Leu Pro Gln Asp Asp Glu Pro Pro Ala Arg
            130                 135                 140 cct ccc cct cct ccc ccg gcc agc gtg agc ccc cag gca gag ccc gtg      540
Pro Pro Pro Pro Pro Pro Ala Ser Val Ser Pro Gln Ala Glu Pro Val
        145                 150                 155 tgg acc ccg cca gcc ccg gct ccc gcc gcg ccc ccc tcc acc ccg gcc      588
Trp Thr Pro Pro Ala Pro Ala Pro Ala Ala Pro Pro Ser Thr Pro Ala
        160                 165                 170 gcg ccc aag cgc agg ggc tcc tcg ggc tca gtg gtt gtt gac ctc ctg      636
Ala Pro Lys Arg Arg Gly Ser Ser Gly Ser Val Val Val Asp Leu Leu
175                 180                 185                 190 tac tgg aga gac att aag aag act gga gtg gtg ttt ggt gcc agc cta      684
Tyr Trp Arg Asp Ile Lys Lys Thr Gly Val Val Phe Gly Ala Ser Leu
                195                 200                 205 ttc ctg ctg ctt tca ttg aca gta ttc agc att gtg agc gta aca gcc      732
Phe Leu Leu Leu Ser Leu Thr Val Phe Ser Ile Val Ser Val Thr Ala
            210                 215                 220 tac att gcc ttg gcc ctg ctc tct gtg acc atc agc ttt agg ata tac      780
Tyr Ile Ala Leu Ala Leu Leu Ser Val Thr Ile Ser Phe Arg Ile Tyr
        225                 230                 235 aag ggt gtg atc caa gct atc cag aaa tca gat gaa ggc cac cca ttc      828
Lys Gly Val Ile Gln Ala Ile Gln Lys Ser Asp Glu Gly His Pro Phe
        240                 245                 250 agg gca tat ctg gaa tct gaa gtt gct ata tct gag gag ttg gtt cag      876
Arg Ala Tyr Leu Glu Ser Glu Val Ala Ile Ser Glu Glu Leu Val Gln
255                 260                 265                 270 aag tac agt aat tct gct ctt ggt cat gtg aac tgc acg ata aag gaa      924
Lys Tyr Ser Asn Ser Ala Leu Gly His Val Asn Cys Thr Ile Lys Glu
                275                 280                 285 ctc agg cgc ctc ttc tta gtt gat gat tta gtt gat tct ctg aag ttt      972
Leu Arg Arg Leu Phe Leu Val Asp Asp Leu Val Asp Ser Leu Lys Phe
            290                 295                 300 gca gtg ttg atg tgg gta ttt acc tat gtt ggt gcc ttg ttt aat ggt     1020
Ala Val Leu Met Trp Val Phe Thr Tyr Val Gly Ala Leu Phe Asn Gly
```

```
                305              310              315
ctg aca cta ctg att ttg gct ctc att tca ctc ttc agt gtt cct gtt   1068
Leu Thr Leu Leu Ile Leu Ala Leu Ile Ser Leu Phe Ser Val Pro Val
    320                  325                 330 att tat gaa cgg cat cag gca cag ata gat cat tat cta gga ctt gca   1116
Ile Tyr Glu Arg His Gln Ala Gln Ile Asp His Tyr Leu Gly Leu Ala
335                 340                 345                 350 aat aag aat gtt aaa gat gct atg gct aaa atc caa gca aaa atc cct   1164
Asn Lys Asn Val Lys Asp Ala Met Ala Lys Ile Gln Ala Lys Ile Pro
                355                 360                 365 gga ttg aag cgc aaa gct gaa tga aaacgcccaa ataattagt aggagttcat   1218
Gly Leu Lys Arg Lys Ala Glu
                370 ctttaaaggg gatattcatt tgattatacg ggggagggtc agggaagaac gaaccttgac   1278
gttgcagtgc agtttcacag atcgttgtta gatctttatt tttagccatg cactgttgtg   1338
aggaaaaatt acctgtcttg actgccatgt gttcatcatc ttaagtattg taagctgcta   1398
tgtatggatt taaaccgtaa tcatatcttt ttcctatcta tctgaggcac tggtggaata   1458
aaaaacctgt atattttact tgttgcaga tagtcttgcc gcatcttggc aagttgcaga   1518
gatggtggag ctagaaaaaa aaaaaaaaaa aagccctttt cagtttgtgc actgtgtatg   1578
gtccgtgtag attgatgcag attttctgaa atgaaatgtt tgtttagacg agatcatacc   1638
ggtaaagcag gaatgacaaa gcttagacct ttaccttcca gccaccccac agtgcttgat   1698
atttcagagt cagtcattgg ttatacatgt gtagttccaa agcacataag ctagaagaag   1758
aaatatttct aggagcacta ccatctgttt tcaacatgaa atgccacaca catagaactc   1818
caacatcaat tcattgcac agactgactg tagttaattt tgtcacagaa tctatggact   1878
gaatctaatg cttccaaaaa tgttgtttgt ttgcaaatat caaacattgt tatgcaagaa   1938
attattaatt acaaaatgaa gatttatacc attgtggttt aagctgtact gaactaaatc   1998
tgtggaatgc attgtgaact gtaaaagcaa agtatcaata aagcttatag actt          2052
```

<210> SEQ ID NO 4
<211> LENGTH: 373
<212> TYPE: PRT
<213> ORGANISM: Homo sapiens

<400> SEQUENCE: 4

```
Met Glu Asp Leu Asp Gln Ser Pro Leu Val Ser Ser Asp Ser Pro
1               5                   10                  15

Pro Arg Pro Gln Pro Ala Phe Lys Tyr Gln Phe Val Arg Glu Pro Glu
                20                  25                  30

Asp Glu Glu Glu Glu Glu Glu Glu Glu Glu Asp Glu Asp Glu Asp
            35                  40                  45

Leu Glu Glu Leu Glu Val Leu Glu Arg Lys Pro Ala Ala Gly Leu Ser
    50                  55                  60

Ala Ala Pro Val Pro Thr Ala Pro Ala Ala Gly Ala Pro Leu Met Asp
65                  70                  75                  80

Phe Gly Asn Asp Phe Val Pro Pro Ala Pro Arg Gly Pro Leu Pro Ala
                85                  90                  95

Ala Pro Pro Val Ala Pro Glu Arg Gln Pro Cys Trp Asp Pro Ser Pro
                100                 105                 110

Val Ser Ser Thr Val Pro Ala Pro Ser Pro Leu Ser Ala Ala Ala Val
            115                 120                 125

Ser Pro Ser Lys Leu Pro Gln Asp Asp Glu Pro Pro Ala Arg Pro Pro
```

-continued

```
                130                 135                 140
Pro Pro Pro Ala Ser Val Ser Pro Gln Ala Glu Pro Val Trp Thr
145                 150                 155                 160

Pro Pro Ala Pro Ala Ala Pro Pro Ser Thr Pro Ala Ala Pro
                165                 170                 175

Lys Arg Arg Gly Ser Ser Gly Ser Val Val Asp Leu Leu Tyr Trp
                180                 185                 190

Arg Asp Ile Lys Lys Thr Gly Val Val Phe Gly Ala Ser Leu Phe Leu
                195                 200                 205

Leu Leu Ser Leu Thr Val Phe Ser Ile Val Ser Val Thr Ala Tyr Ile
210                 215                 220

Ala Leu Ala Leu Leu Ser Val Thr Ile Ser Phe Arg Ile Tyr Lys Gly
225                 230                 235                 240

Val Ile Gln Ala Ile Gln Lys Ser Asp Glu Gly His Pro Phe Arg Ala
                245                 250                 255

Tyr Leu Glu Ser Glu Val Ala Ile Ser Glu Glu Leu Val Gln Lys Tyr
                260                 265                 270

Ser Asn Ser Ala Leu Gly His Val Asn Cys Thr Ile Lys Glu Leu Arg
                275                 280                 285

Arg Leu Phe Leu Val Asp Asp Leu Val Asp Ser Leu Lys Phe Ala Val
290                 295                 300

Leu Met Trp Val Phe Thr Tyr Val Gly Ala Leu Phe Asn Gly Leu Thr
305                 310                 315                 320

Leu Leu Ile Leu Ala Leu Ile Ser Leu Phe Ser Val Pro Val Ile Tyr
                325                 330                 335

Glu Arg His Gln Ala Gln Ile Asp His Tyr Leu Gly Leu Ala Asn Lys
                340                 345                 350

Asn Val Lys Asp Ala Met Ala Lys Ile Gln Ala Lys Ile Pro Gly Leu
                355                 360                 365

Lys Arg Lys Ala Glu
    370

<210> SEQ ID NO 5
<211> LENGTH: 13
<212> TYPE: PRT
<213> ORGANISM: Homo sapiens

<400> SEQUENCE: 5

Gly Pro Leu Pro Ala Ala Pro Pro Val Ala Pro Glu Arg
1               5                   10

<210> SEQ ID NO 6
<211> LENGTH: 14
<212> TYPE: PRT
<213> ORGANISM: Homo sapiens

<400> SEQUENCE: 6

Gly Ser Ser Gly Ser Val Val Asp Leu Leu Tyr Trp Arg
1               5                   10

<210> SEQ ID NO 7
<211> LENGTH: 14
<212> TYPE: PRT
<213> ORGANISM: Homo sapiens

<400> SEQUENCE: 7

Tyr Ser Asn Ser Ala Leu Gly His Val Asn Cys Thr Ile Lys
1               5                   10
```

<210> SEQ ID NO 8
<211> LENGTH: 3579
<212> TYPE: DNA
<213> ORGANISM: Homo sapiens
<220> FEATURE:
<221> NAME/KEY: CDS
<222> LOCATION: (1)..(3579)

<400> SEQUENCE: 8

| | | |
|---|---|---|
| atg gaa gac ctg gac cag tct cct ctg gtc tcg tcc tcg gac agc cca<br>Met Glu Asp Leu Asp Gln Ser Pro Leu Val Ser Ser Ser Asp Ser Pro<br>1                      5                   10                 15 | 48 |
| ccc cgg ccg cag ccc gcg ttc aag tac cag ttc gtg agg gag ccc gag<br>Pro Arg Pro Gln Pro Ala Phe Lys Tyr Gln Phe Val Arg Glu Pro Glu<br>                20                   25                   30 | 96 |
| gac gag gag gaa gaa gag gag gag gag gag gac gag gac gaa gac<br>Asp Glu Glu Glu Glu Glu Glu Glu Glu Glu Asp Glu Asp Glu Asp<br>                      35                   40                   45 | 144 |
| ctg gag gag ctg gag gtg ctg gag agg aag ccc gcc gcc ggg ctg tcc<br>Leu Glu Glu Leu Glu Val Leu Glu Arg Lys Pro Ala Ala Gly Leu Ser<br>50                      55                   60 | 192 |
| gcg gcc cca gtg ccc acc gcc cct gcc gcc ggc gcg ccc ctg atg gac<br>Ala Ala Pro Val Pro Thr Ala Pro Ala Ala Gly Ala Pro Leu Met Asp<br>65                      70                   75                   80 | 240 |
| ttc gga aat gac ttc gtg ccg ccg gcg ccc cgg gga ccc ctg ccg gcc<br>Phe Gly Asn Asp Phe Val Pro Pro Ala Pro Arg Gly Pro Leu Pro Ala<br>                          85                   90                   95 | 288 |
| gct ccc ccc gtc gcc ccg gag cgg cag ccg tct tgg gac ccg agc ccg<br>Ala Pro Pro Val Ala Pro Glu Arg Gln Pro Ser Trp Asp Pro Ser Pro<br>                  100                 105                 110 | 336 |
| gtg tcg tcg acc gtg ccc gcg cca tcc ccg ctg tct gct gcc gca gtc<br>Val Ser Ser Thr Val Pro Ala Pro Ser Pro Leu Ser Ala Ala Ala Val<br>                115                 120               125 | 384 |
| tcg ccc tcc aag ctc cct gag gac gac gag cct ccg gcc cgg cct ccc<br>Ser Pro Ser Lys Leu Pro Glu Asp Asp Glu Pro Pro Ala Arg Pro Pro<br>        130                 135                 140 | 432 |
| cct cct ccc ccg gcc agc gtg agc ccc cag gca gag ccc gtg tgg acc<br>Pro Pro Pro Pro Ala Ser Val Ser Pro Gln Ala Glu Pro Val Trp Thr<br>145                    150                 155                 160 | 480 |
| ccg cca gcc ccg gct ccc gcc gcg ccc ccc tcc acc ccg gcc gcg ccc<br>Pro Pro Ala Pro Ala Pro Ala Ala Pro Pro Ser Thr Pro Ala Ala Pro<br>                165                 170               175 | 528 |
| aag cgc agg ggc tcc tcg ggc tca gtg gat gag acc ctt ttt gct ctt<br>Lys Arg Arg Gly Ser Ser Gly Ser Val Asp Glu Thr Leu Phe Ala Leu<br>                180                 185               190 | 576 |
| cct gct gca tct gag cct gtg ata cgc tcc tct gca gaa aat atg gac<br>Pro Ala Ala Ser Glu Pro Val Ile Arg Ser Ser Ala Glu Asn Met Asp<br>        195                 200                 205 | 624 |
| ttg aag gag cag cca ggt aac act att tcg gct ggt caa gag gat ttc<br>Leu Lys Glu Gln Pro Gly Asn Thr Ile Ser Ala Gly Gln Glu Asp Phe<br>        210                 215                 220 | 672 |
| cca tct gtc ctg ctt gaa act gct gct tct ctt cct tct ctg tct cct<br>Pro Ser Val Leu Leu Glu Thr Ala Ala Ser Leu Pro Ser Leu Ser Pro<br>225                    230                 235                 240 | 720 |
| ctc tca gcc gct tct ttc aaa gaa cat gaa tac ctt ggt aat ttg tca<br>Leu Ser Ala Ala Ser Phe Lys Glu His Glu Tyr Leu Gly Asn Leu Ser<br>                245                 250               255 | 768 |
| aca gta tta ccc act gaa gga aca ctt caa gaa aat gtc agt gaa gct<br>Thr Val Leu Pro Thr Glu Gly Thr Leu Gln Glu Asn Val Ser Glu Ala<br>                    260                 265               270 | 816 |

-continued

```
tct aaa gag gtc tca gag aag gca aaa act cta ctc ata gat aga gat    864
Ser Lys Glu Val Ser Glu Lys Ala Lys Thr Leu Leu Ile Asp Arg Asp
        275                 280                 285 tta aca gag ttt tca gaa tta gaa tac tca gaa atg gga tca tcg ttc    912
Leu Thr Glu Phe Ser Glu Leu Glu Tyr Ser Glu Met Gly Ser Ser Phe
    290                 295                 300 agt gtc tct cca aaa gca gaa tct gcc gta ata gta gca aat cct agg    960
Ser Val Ser Pro Lys Ala Glu Ser Ala Val Ile Val Ala Asn Pro Arg
305                 310                 315                 320 gaa gaa ata atc gtg aaa aat aaa gat gaa gaa gag aag tta gtt agt   1008
Glu Glu Ile Ile Val Lys Asn Lys Asp Glu Glu Glu Lys Leu Val Ser
                325                 330                 335 aat aac atc ctt cat aat caa caa gag tta cct aca gct ctt act aaa   1056
Asn Asn Ile Leu His Asn Gln Gln Glu Leu Pro Thr Ala Leu Thr Lys
            340                 345                 350 ttg gtt aaa gag gat gaa gtt gtg tct tca gaa aaa gca aaa gac agt   1104
Leu Val Lys Glu Asp Glu Val Val Ser Ser Glu Lys Ala Lys Asp Ser
        355                 360                 365 ttt aat gaa aag aga gtt gca gtg gaa gct cct atg agg gag gaa tat   1152
Phe Asn Glu Lys Arg Val Ala Val Glu Ala Pro Met Arg Glu Glu Tyr
    370                 375                 380 gca gac ttc aaa cca ttt gag cga gta tgg gaa gtg aaa gat agt aag   1200
Ala Asp Phe Lys Pro Phe Glu Arg Val Trp Glu Val Lys Asp Ser Lys
385                 390                 395                 400 gaa gat agt gat atg ttg gct gct gga ggt aaa atc gag agc aac ttg   1248
Glu Asp Ser Asp Met Leu Ala Ala Gly Gly Lys Ile Glu Ser Asn Leu
                405                 410                 415 gaa agt aaa gtg gat aaa aaa tgt ttt gca gat agc ctt gag caa act   1296
Glu Ser Lys Val Asp Lys Lys Cys Phe Ala Asp Ser Leu Glu Gln Thr
            420                 425                 430 aat cac gaa aaa gat agt gag agt agt aat gat gat act tct ttc ccc   1344
Asn His Glu Lys Asp Ser Glu Ser Ser Asn Asp Asp Thr Ser Phe Pro
        435                 440                 445 agt acg cca gaa ggt ata aag gat cgt cca gga gca tat atc aca tgt   1392
Ser Thr Pro Glu Gly Ile Lys Asp Arg Pro Gly Ala Tyr Ile Thr Cys
    450                 455                 460 gct ccc ttt aac cca gca gca act gag agc att gca aca aac att ttt   1440
Ala Pro Phe Asn Pro Ala Ala Thr Glu Ser Ile Ala Thr Asn Ile Phe
465                 470                 475                 480 cct ttg tta gga gat cct act tca gaa aat aag acc gat gaa aaa aaa   1488
Pro Leu Leu Gly Asp Pro Thr Ser Glu Asn Lys Thr Asp Glu Lys Lys
                485                 490                 495 ata gaa gaa aag aag gcc caa ata gta aca gag aag aat act agc acc   1536
Ile Glu Glu Lys Lys Ala Gln Ile Val Thr Glu Lys Asn Thr Ser Thr
            500                 505                 510 aaa aca tca aac cct ttt ctt gta gca gca cag gat tct gag aca gat   1584
Lys Thr Ser Asn Pro Phe Leu Val Ala Ala Gln Asp Ser Glu Thr Asp
        515                 520                 525 tat gtc aca aca gat aat tta aca aag gtg act gag gaa gtc gtg gca   1632
Tyr Val Thr Thr Asp Asn Leu Thr Lys Val Thr Glu Glu Val Val Ala
    530                 535                 540 aac atg cct gaa ggc ctg act cca gat tta gta cag gaa gca tgt gaa   1680
Asn Met Pro Glu Gly Leu Thr Pro Asp Leu Val Gln Glu Ala Cys Glu
545                 550                 555                 560 agt gaa ttg aat gaa gtt act ggt aca aag att gct tat gaa aca aaa   1728
Ser Glu Leu Asn Glu Val Thr Gly Thr Lys Ile Ala Tyr Glu Thr Lys
                565                 570                 575 atg gac ttg gtt caa aca tca gaa gtt atg caa gag tca ctc tat cct   1776
Met Asp Leu Val Gln Thr Ser Glu Val Met Gln Glu Ser Leu Tyr Pro
```

```
                       580                 585                 590
gca gca cag ctt tgc cca tca ttt gaa gag tca gaa gct act cct tca      1824
Ala Ala Gln Leu Cys Pro Ser Phe Glu Glu Ser Glu Ala Thr Pro Ser
        595                 600                 605 cca gtt ttg cct gac att gtt atg gaa gca cca ttg aat tct gca gtt      1872
Pro Val Leu Pro Asp Ile Val Met Glu Ala Pro Leu Asn Ser Ala Val
610                 615                 620 cct agt gct ggt gct tcc gtg ata cag ccc agc tca tca cca tta gaa      1920
Pro Ser Ala Gly Ala Ser Val Ile Gln Pro Ser Ser Pro Leu Glu
625                 630                 635                 640 gct tct tca gtt aat tat gaa agc ata aaa cat gag cct gaa aac ccc      1968
Ala Ser Ser Val Asn Tyr Glu Ser Ile Lys His Glu Pro Glu Asn Pro
                645                 650                 655 cca cca tat gaa gag gcc atg agt gta tca cta aaa aaa gta tca gga      2016
Pro Pro Tyr Glu Glu Ala Met Ser Val Ser Leu Lys Lys Val Ser Gly
            660                 665                 670 ata aag gaa gaa att aaa gag cct gaa aat att aat gca gct ctt caa      2064
Ile Lys Glu Glu Ile Lys Glu Pro Glu Asn Ile Asn Ala Ala Leu Gln
        675                 680                 685 gaa aca gaa gct cct tat ata tct att gca tgt gat tta att aaa gaa      2112
Glu Thr Glu Ala Pro Tyr Ile Ser Ile Ala Cys Asp Leu Ile Lys Glu
690                 695                 700 aca aag ctt tct gct gaa cca gct ccg gat ttc tct gat tat tca gaa      2160
Thr Lys Leu Ser Ala Glu Pro Ala Pro Asp Phe Ser Asp Tyr Ser Glu
705                 710                 715                 720 atg gca aaa gtt gaa cag cca gtg cct gat cat tct gag cta gtt gaa      2208
Met Ala Lys Val Glu Gln Pro Val Pro Asp His Ser Glu Leu Val Glu
                725                 730                 735 gat tcc tca cct gat tct gaa cca gtt gac tta ttt agt gat gat tca      2256
Asp Ser Ser Pro Asp Ser Glu Pro Val Asp Leu Phe Ser Asp Asp Ser
            740                 745                 750 ata cct gac gtt cca caa aaa caa gat gaa act gtg atg ctt gtg aaa      2304
Ile Pro Asp Val Pro Gln Lys Gln Asp Glu Thr Val Met Leu Val Lys
        755                 760                 765 gaa agt ctc act gag act tca ttt gag tca atg ata gaa tat gaa aat      2352
Glu Ser Leu Thr Glu Thr Ser Phe Glu Ser Met Ile Glu Tyr Glu Asn
770                 775                 780 aag gaa aaa ctc agt gct ttg cca cct gag gga gga aag cca tat ttg      2400
Lys Glu Lys Leu Ser Ala Leu Pro Pro Glu Gly Gly Lys Pro Tyr Leu
785                 790                 795                 800 gaa tct ttt aag ctc agt tta gat aac aca aaa gat acc ctg tta cct      2448
Glu Ser Phe Lys Leu Ser Leu Asp Asn Thr Lys Asp Thr Leu Leu Pro
                805                 810                 815 gat gaa gtt tca aca ttg agc aaa aag gag aaa att cct ttg cag atg      2496
Asp Glu Val Ser Thr Leu Ser Lys Lys Glu Lys Ile Pro Leu Gln Met
            820                 825                 830 gag gag ctc agt act gca gtt tat tca aat gat gac tta ttt att tct      2544
Glu Glu Leu Ser Thr Ala Val Tyr Ser Asn Asp Asp Leu Phe Ile Ser
        835                 840                 845 aag gaa gca cag ata aga gaa act gaa acg ttt tca gat tca tct cca      2592
Lys Glu Ala Gln Ile Arg Glu Thr Glu Thr Phe Ser Asp Ser Ser Pro
850                 855                 860 att gaa att ata gat gag ttc cct aca ttg atc agt tct aaa act gat      2640
Ile Glu Ile Ile Asp Glu Phe Pro Thr Leu Ile Ser Ser Lys Thr Asp
865                 870                 875                 880 tca ttt tct aaa tta gcc agg gaa tat act gac cta gaa gta tcc cac      2688
Ser Phe Ser Lys Leu Ala Arg Glu Tyr Thr Asp Leu Glu Val Ser His
                885                 890                 895 aaa agt gaa att gct aat gcc ccg gat gga gct ggg tca ttg cct tgc      2736
```

-continued

```
                Lys Ser Glu Ile Ala Asn Ala Pro Asp Gly Ala Gly Ser Leu Pro Cys
                        900                 905                 910 aca gaa ttg ccc cat gac ctt tct ttg aag aac ata caa ccc aaa gtt         2784
Thr Glu Leu Pro His Asp Leu Ser Leu Lys Asn Ile Gln Pro Lys Val
            915                 920                 925 gaa gag aaa atc agt ttc tca gat gac ttt tct aaa aat ggg tct gct         2832
Glu Glu Lys Ile Ser Phe Ser Asp Asp Phe Ser Lys Asn Gly Ser Ala
    930                 935                 940 aca tca aag gtg ctc tta ttg cct cca gat gtt tct gct ttg gcc act         2880
Thr Ser Lys Val Leu Leu Leu Pro Pro Asp Val Ser Ala Leu Ala Thr
945                 950                 955                 960 caa gca gag ata gag agc ata gtt aaa ccc aaa gtt ctt gtg aaa gaa         2928
Gln Ala Glu Ile Glu Ser Ile Val Lys Pro Lys Val Leu Val Lys Glu
                965                 970                 975 gct gag aaa aaa ctt cct tcc gat aca gaa aaa gag gac aga tca cca         2976
Ala Glu Lys Lys Leu Pro Ser Asp Thr Glu Lys Glu Asp Arg Ser Pro
            980                 985                 990 tct gct ata ttt tca gca gag ctg agt aaa act tca gtt gtt gac ctc        3024
Ser Ala Ile Phe Ser Ala Glu Leu Ser Lys Thr Ser Val Val Asp Leu
        995                 1000                1005 ctg tac tgg aga gac att aag aag act gga gtg gtg ttt ggt gcc            3069
Leu Tyr Trp Arg Asp Ile Lys Lys Thr Gly Val Val Phe Gly Ala
    1010                1015                1020 agc cta ttc ctg ctg ctt tca ttg aca gta ttc agc att gtg agc            3114
Ser Leu Phe Leu Leu Leu Ser Leu Thr Val Phe Ser Ile Val Ser
    1025                1030                1035 gta aca gcc tac att gcc ttg gcc ctg ctc tct gtg acc atc agc            3159
Val Thr Ala Tyr Ile Ala Leu Ala Leu Leu Ser Val Thr Ile Ser
    1040                1045                1050 ttt agg ata tac aag ggt gtg atc caa gct atc cag aaa tca gat            3204
Phe Arg Ile Tyr Lys Gly Val Ile Gln Ala Ile Gln Lys Ser Asp
    1055                1060                1065 gaa ggc cac cca ttc agg gca tat ctg gaa tct gaa gtt gct ata            3249
Glu Gly His Pro Phe Arg Ala Tyr Leu Glu Ser Glu Val Ala Ile
    1070                1075                1080 tct gag gag ttg gtt cag aag tac agt aat tct gct ctt ggt cat            3294
Ser Glu Glu Leu Val Gln Lys Tyr Ser Asn Ser Ala Leu Gly His
    1085                1090                1095 gtg aac tgc acg ata aag gaa ctc agg cgc ctc ttc tta gtt gat            3339
Val Asn Cys Thr Ile Lys Glu Leu Arg Arg Leu Phe Leu Val Asp
    1100                1105                1110 gat tta gtt gat tct ctg aag ttt gca gtg ttg atg tgg gta ttt            3384
Asp Leu Val Asp Ser Leu Lys Phe Ala Val Leu Met Trp Val Phe
    1115                1120                1125 acc tat gtt ggt gcc ttg ttt aat ggt ctg aca cta ctg att ttg            3429
Thr Tyr Val Gly Ala Leu Phe Asn Gly Leu Thr Leu Leu Ile Leu
    1130                1135                1140 gct ctc att tca ctc ttc agt gtt cct gtt att tat gaa cgg cat            3474
Ala Leu Ile Ser Leu Phe Ser Val Pro Val Ile Tyr Glu Arg His
    1145                1150                1155 cag gcg cag ata gat cat tat cta gga ctt gca aat aag aat gtt            3519
Gln Ala Gln Ile Asp His Tyr Leu Gly Leu Ala Asn Lys Asn Val
    1160                1165                1170 aaa gat gct atg gct aaa atc caa gca aaa atc cct gga ttg aag            3564
Lys Asp Ala Met Ala Lys Ile Gln Ala Lys Ile Pro Gly Leu Lys
    1175                1180                1185 cgc aaa gct gaa tga                                                    3579
Arg Lys Ala Glu
    1190
```

<210> SEQ ID NO 9
<211> LENGTH: 1192
<212> TYPE: PRT
<213> ORGANISM: Homo sapiens

<400> SEQUENCE: 9

```
Met Glu Asp Leu Asp Gln Ser Pro Leu Val Ser Ser Asp Ser Pro
 1               5                  10                  15

Pro Arg Pro Gln Pro Ala Phe Lys Tyr Gln Phe Val Arg Glu Pro Glu
                20                  25                  30

Asp Glu Glu Glu Glu Glu Glu Glu Glu Asp Glu Asp Glu Asp
            35                  40                  45

Leu Glu Glu Leu Glu Val Leu Glu Arg Lys Pro Ala Ala Gly Leu Ser
        50                  55                  60

Ala Ala Pro Val Pro Thr Ala Pro Ala Ala Gly Ala Pro Leu Met Asp
65                  70                  75                  80

Phe Gly Asn Asp Phe Val Pro Pro Ala Pro Arg Gly Pro Leu Pro Ala
                85                  90                  95

Ala Pro Pro Val Ala Pro Glu Arg Gln Pro Ser Trp Asp Pro Ser Pro
                100                 105                 110

Val Ser Ser Thr Val Pro Ala Pro Ser Pro Leu Ser Ala Ala Ala Val
            115                 120                 125

Ser Pro Ser Lys Leu Pro Glu Asp Asp Glu Pro Pro Ala Arg Pro Pro
        130                 135                 140

Pro Pro Pro Pro Ala Ser Val Ser Pro Gln Ala Glu Pro Val Trp Thr
145                 150                 155                 160

Pro Pro Ala Pro Ala Pro Ala Ala Pro Pro Ser Thr Pro Ala Ala Pro
                165                 170                 175

Lys Arg Arg Gly Ser Ser Gly Ser Val Asp Glu Thr Leu Phe Ala Leu
                180                 185                 190

Pro Ala Ala Ser Glu Pro Val Ile Arg Ser Ser Ala Glu Asn Met Asp
            195                 200                 205

Leu Lys Glu Gln Pro Gly Asn Thr Ile Ser Ala Gly Gln Glu Asp Phe
        210                 215                 220

Pro Ser Val Leu Leu Glu Thr Ala Ala Ser Leu Pro Ser Leu Ser Pro
225                 230                 235                 240

Leu Ser Ala Ala Ser Phe Lys Glu His Glu Tyr Leu Gly Asn Leu Ser
                245                 250                 255

Thr Val Leu Pro Thr Glu Gly Thr Leu Gln Glu Asn Val Ser Glu Ala
                260                 265                 270

Ser Lys Glu Val Ser Glu Lys Ala Lys Thr Leu Leu Ile Asp Arg Asp
        275                 280                 285

Leu Thr Glu Phe Ser Glu Leu Glu Tyr Ser Glu Met Gly Ser Ser Phe
        290                 295                 300

Ser Val Ser Pro Lys Ala Glu Ser Ala Val Ile Val Ala Asn Pro Arg
305                 310                 315                 320

Glu Glu Ile Ile Val Lys Asn Lys Asp Glu Glu Lys Leu Val Ser
                325                 330                 335

Asn Asn Ile Leu His Asn Gln Gln Glu Leu Pro Thr Ala Leu Thr Lys
            340                 345                 350

Leu Val Lys Glu Asp Glu Val Val Ser Ser Glu Lys Ala Lys Asp Ser
        355                 360                 365

Phe Asn Glu Lys Arg Val Ala Val Glu Ala Pro Met Arg Glu Glu Tyr
        370                 375                 380
```

-continued

```
Ala Asp Phe Lys Pro Phe Glu Arg Val Trp Glu Val Lys Asp Ser Lys
385                 390                 395                 400

Glu Asp Ser Asp Met Leu Ala Ala Gly Gly Lys Ile Glu Ser Asn Leu
            405                 410                 415

Glu Ser Lys Val Asp Lys Lys Cys Phe Ala Asp Ser Leu Glu Gln Thr
            420                 425                 430

Asn His Glu Lys Asp Ser Glu Ser Ser Asn Asp Asp Thr Ser Phe Pro
        435                 440                 445

Ser Thr Pro Glu Gly Ile Lys Asp Arg Pro Gly Ala Tyr Ile Thr Cys
    450                 455                 460

Ala Pro Phe Asn Pro Ala Ala Thr Glu Ser Ile Ala Thr Asn Ile Phe
465                 470                 475                 480

Pro Leu Leu Gly Asp Pro Thr Ser Glu Asn Lys Thr Asp Glu Lys Lys
                485                 490                 495

Ile Glu Glu Lys Lys Ala Gln Ile Val Thr Glu Lys Asn Thr Ser Thr
                500                 505                 510

Lys Thr Ser Asn Pro Phe Leu Val Ala Ala Gln Asp Ser Glu Thr Asp
        515                 520                 525

Tyr Val Thr Thr Asp Asn Leu Thr Lys Val Thr Glu Glu Val Val Ala
    530                 535                 540

Asn Met Pro Glu Gly Leu Thr Pro Asp Leu Val Gln Glu Ala Cys Glu
545                 550                 555                 560

Ser Glu Leu Asn Glu Val Thr Gly Thr Lys Ile Ala Tyr Glu Thr Lys
                565                 570                 575

Met Asp Leu Val Gln Thr Ser Glu Val Met Gln Glu Ser Leu Tyr Pro
                580                 585                 590

Ala Ala Gln Leu Cys Pro Ser Phe Glu Glu Ser Glu Ala Thr Pro Ser
        595                 600                 605

Pro Val Leu Pro Asp Ile Val Met Glu Ala Pro Leu Asn Ser Ala Val
    610                 615                 620

Pro Ser Ala Gly Ala Ser Val Ile Gln Pro Ser Ser Pro Leu Glu
625                 630                 635                 640

Ala Ser Ser Val Asn Tyr Glu Ser Ile Lys His Glu Pro Glu Asn Pro
                645                 650                 655

Pro Pro Tyr Glu Glu Ala Met Ser Val Ser Leu Lys Lys Val Ser Gly
                660                 665                 670

Ile Lys Glu Glu Ile Lys Glu Pro Glu Asn Ile Asn Ala Ala Leu Gln
        675                 680                 685

Glu Thr Glu Ala Pro Tyr Ile Ser Ile Ala Cys Asp Leu Ile Lys Glu
    690                 695                 700

Thr Lys Leu Ser Ala Glu Pro Ala Pro Asp Phe Ser Asp Tyr Ser Glu
705                 710                 715                 720

Met Ala Lys Val Glu Gln Pro Val Pro Asp His Ser Glu Leu Val Glu
                725                 730                 735

Asp Ser Ser Pro Asp Ser Glu Pro Val Asp Leu Phe Ser Asp Asp Ser
            740                 745                 750

Ile Pro Asp Val Pro Gln Lys Gln Asp Glu Thr Val Met Leu Val Lys
        755                 760                 765

Glu Ser Leu Thr Glu Thr Ser Phe Glu Ser Met Ile Glu Tyr Glu Asn
    770                 775                 780

Lys Glu Lys Leu Ser Ala Leu Pro Pro Glu Gly Gly Lys Pro Tyr Leu
785                 790                 795                 800
```

-continued

```
Glu Ser Phe Lys Leu Ser Leu Asp Asn Thr Lys Asp Thr Leu Leu Pro
                805                 810                 815

Asp Glu Val Ser Thr Leu Ser Lys Lys Glu Lys Ile Pro Leu Gln Met
            820                 825                 830

Glu Glu Leu Ser Thr Ala Val Tyr Ser Asn Asp Asp Leu Phe Ile Ser
            835                 840                 845

Lys Glu Ala Gln Ile Arg Glu Thr Glu Thr Phe Ser Asp Ser Ser Pro
850                 855                 860

Ile Glu Ile Ile Asp Glu Phe Pro Thr Leu Ile Ser Ser Lys Thr Asp
865                 870                 875                 880

Ser Phe Ser Lys Leu Ala Arg Glu Tyr Thr Asp Leu Glu Val Ser His
                885                 890                 895

Lys Ser Glu Ile Ala Asn Ala Pro Asp Gly Ala Gly Ser Leu Pro Cys
                900                 905                 910

Thr Glu Leu Pro His Asp Leu Ser Leu Lys Asn Ile Gln Pro Lys Val
                915                 920                 925

Glu Glu Lys Ile Ser Phe Ser Asp Asp Phe Ser Lys Asn Gly Ser Ala
930                 935                 940

Thr Ser Lys Val Leu Leu Pro Pro Asp Val Ser Ala Leu Ala Thr
945                 950                 955                 960

Gln Ala Glu Ile Glu Ser Ile Val Lys Pro Lys Val Leu Val Lys Glu
                965                 970                 975

Ala Glu Lys Lys Leu Pro Ser Asp Thr Glu Lys Glu Asp Arg Ser Pro
            980                 985                 990

Ser Ala Ile Phe Ser Ala Glu Leu  Ser Lys Thr Ser Val  Val Asp Leu
            995                 1000                1005

Leu Tyr Trp Arg Asp Ile Lys  Lys Thr Gly Val Val  Phe Gly Ala
    1010                1015                1020

Ser Leu Phe Leu Leu Leu Ser  Leu Thr Val Phe Ser  Ile Val Ser
    1025                1030                1035

Val Thr Ala Tyr Ile Ala Leu  Ala Leu Leu Ser Val  Thr Ile Ser
    1040                1045                1050

Phe Arg Ile Tyr Lys Gly Val  Ile Gln Ala Ile Gln  Lys Ser Asp
    1055                1060                1065

Glu Gly His Pro Phe Arg Ala  Tyr Leu Glu Ser Glu  Val Ala Ile
    1070                1075                1080

Ser Glu Glu Leu Val Gln Lys  Tyr Ser Asn Ser Ala  Leu Gly His
    1085                1090                1095

Val Asn Cys Thr Ile Lys Glu  Leu Arg Arg Leu Phe  Leu Val Asp
    1100                1105                1110

Asp Leu Val Asp Ser Leu Lys  Phe Ala Val Leu Met  Trp Val Phe
    1115                1120                1125

Thr Tyr Val Gly Ala Leu Phe  Asn Gly Leu Thr Leu  Leu Ile Leu
    1130                1135                1140

Ala Leu Ile Ser Leu Phe Ser  Val Pro Val Ile Tyr  Glu Arg His
    1145                1150                1155

Gln Ala Gln Ile Asp His Tyr  Leu Gly Leu Ala Asn  Lys Asn Val
    1160                1165                1170

Lys Asp Ala Met Ala Lys Ile  Gln Ala Lys Ile Pro  Gly Leu Lys
    1175                1180                1185

Arg Lys Ala Glu
    1190
```

```
<210> SEQ ID NO 10
<211> LENGTH: 1798
<212> TYPE: DNA
<213> ORGANISM: Homo sapiens
<220> FEATURE:
<221> NAME/KEY: CDS
<222> LOCATION: (215)..(814)

<400> SEQUENCE: 10
```

| | |
|---|---|
| agcctagtta cagattgcac tgcgtcagac tgttccacac ccagaagacg tcaggtgact | 60 |
| tcagtcctgc tgcagttgtg cagcagagga gactgcagac ttcggttgag gaaacgggta | 120 |
| tttcatgtct cagggagtag gtttgtgcag ttacagcttt tctgttggta tgcataatta | 180 |
| ataattggag ctgcaaagca gatcgtgaca agag atg gac ggt cag aag aaa aat | 235 |
|                                               Met Asp Gly Gln Lys Lys Asn<br>                                              1              5 | |
| tgg aag gac aag gtt gtt gac ctc ctg tac tgg aga gac att aag aag<br>Trp Lys Asp Lys Val Val Asp Leu Leu Tyr Trp Arg Asp Ile Lys Lys<br>          10                      15                      20 | 283 |
| act gga gtg gtg ttt ggt gcc agc cta ttc ctg ctt tca ttg aca<br>Thr Gly Val Val Phe Gly Ala Ser Leu Phe Leu Leu Ser Leu Thr<br>    25                      30                      35 | 331 |
| gta ttc agc att gtg agc gta aca gcc tac att gcc ttg gcc ctg ctc<br>Val Phe Ser Ile Val Ser Val Thr Ala Tyr Ile Ala Leu Ala Leu Leu<br>40                      45                      50                      55 | 379 |
| tct gtg acc atc agc ttt agg ata tac aag ggt gtg atc caa gct atc<br>Ser Val Thr Ile Ser Phe Arg Ile Tyr Lys Gly Val Ile Gln Ala Ile<br>                    60                      65                      70 | 427 |
| cag aaa tca gat gaa ggc cac cca ttc agg gca tat ctg gaa tct gaa<br>Gln Lys Ser Asp Glu Gly His Pro Phe Arg Ala Tyr Leu Glu Ser Glu<br>          75                      80                      85 | 475 |
| gtt gct ata tct gag gag ttg gtt cag aag tac agt aat tct gct ctt<br>Val Ala Ile Ser Glu Glu Leu Val Gln Lys Tyr Ser Asn Ser Ala Leu<br>              90                      95                      100 | 523 |
| ggt cat gtg aac tgc acg ata aag gaa ctc agg cgc ctc ttc tta gtt<br>Gly His Val Asn Cys Thr Ile Lys Glu Leu Arg Arg Leu Phe Leu Val<br>105                     110                      115 | 571 |
| gat gat tta gtt gat tct ctg aag ttt gca gtg ttg atg tgg gta ttt<br>Asp Asp Leu Val Asp Ser Leu Lys Phe Ala Val Leu Met Trp Val Phe<br>120                     125                      130                      135 | 619 |
| acc tat gtt ggt gcc ttg ttt aat ggt ctg aca cta ctg att ttg gct<br>Thr Tyr Val Gly Ala Leu Phe Asn Gly Leu Thr Leu Leu Ile Leu Ala<br>                    140                      145                      150 | 667 |
| ctc att tca ctc ctt cag tgt tcc tgt tat tta gaa cgg cat cag gca<br>Leu Ile Ser Leu Leu Gln Cys Ser Cys Tyr Leu Glu Arg His Gln Ala<br>              155                      160                      165 | 715 |
| cag ata gat cat tat cta gga ctt gca aat aag aat gtt aaa gat gct<br>Gln Ile Asp His Tyr Leu Gly Leu Ala Asn Lys Asn Val Lys Asp Ala<br>          170                      175                      180 | 763 |
| atg gct aaa atc caa gca aaa atc cct gga ttg aag cgc aaa gct gaa<br>Met Ala Lys Ile Gln Ala Lys Ile Pro Gly Leu Lys Arg Lys Ala Glu<br>    185                      190                      195 | 811 |
| tga aaacgcccaa aataattagt aggagttcat ctttaaaggg gatattcatt | 864 |
| tgattatacg ggggagggtc aggaagaac gaaccttgac gttgcagtgc agtttcacag | 924 |
| atcgttgtta gatctttatt tttagccatg cactgttgtg aggaaaaatt acctgtcttg | 984 |
| actgccatgt gttcatcatc ttaagtattg taagctgcta tgtatggatt taaaccgtaa | 1044 |
| tcatatcttt ttcctatcta tctgaggcac tggtggaata aaaaacctgt atattttact | 1104 |
| ttgttgcaga tagtcttgcc gcatcttggc aagttgcaga gatggtggag ctagaaaaaa | 1164 |

-continued

```
aaaaaaaaaa gcccttttca gtttgtgcac tgtgtatggt ccgtgtagat tgatgcagat    1224
tttctgaaat gaaatgtttg tttagacgag atcataccgg taaagcagga atgacaaagc    1284
ttgcttttct ggtatgttct aggtgtattg tgacttttac tgttatatta attgccaata    1344
taagtaaata tagattatat atgtatagtg tttcacaaag cttagacctt taccttccag    1404
ccacccacag gtgcttgata tttcagagtc agtcattggt tatacatgtg tagttccaaa    1464
gcacataagc tagaagaaga aatatttcta ggagcactac catcgttttc aacatgaaat    1524
gccacacaca tagaactcca acaacatcaa tttcattgca cagactgact gtagttaatt    1584
ttgtcacagg atctatggac tgaatctaat gcttccaaaa atgttgtttg tttgcaaata    1644
tcaaacattg ttatgcaaga aattattaat tacaaaatga agatttatac cattgtggtt    1704
taagctgtac tgaactaaat ctgtggaagg cattgtaaac tgtaaaagca agtatcaat     1764 aaagcttata gacccaaaac gaaaaaaaaa aaaa                                1798
```

<210> SEQ ID NO 11
<211> LENGTH: 199
<212> TYPE: PRT
<213> ORGANISM: Homo sapiens

<400> SEQUENCE: 11

```
Met Asp Gly Gln Lys Lys Asn Trp Lys Asp Lys Val Val Asp Leu Leu
1               5                   10                  15

Tyr Trp Arg Asp Ile Lys Lys Thr Gly Val Val Phe Gly Ala Ser Leu
            20                  25                  30

Phe Leu Leu Leu Ser Leu Thr Val Phe Ser Ile Val Ser Val Thr Ala
        35                  40                  45

Tyr Ile Ala Leu Ala Leu Leu Ser Val Thr Ile Ser Phe Arg Ile Tyr
    50                  55                  60

Lys Gly Val Ile Gln Ala Ile Gln Lys Ser Asp Glu Gly His Pro Phe
65                  70                  75                  80

Arg Ala Tyr Leu Glu Ser Glu Val Ala Ile Ser Glu Glu Leu Val Gln
                85                  90                  95

Lys Tyr Ser Asn Ser Ala Leu Gly His Val Asn Cys Thr Ile Lys Glu
            100                 105                 110

Leu Arg Arg Leu Phe Leu Val Asp Asp Leu Val Asp Ser Leu Lys Phe
        115                 120                 125

Ala Val Leu Met Trp Val Phe Thr Tyr Val Gly Ala Leu Phe Asn Gly
    130                 135                 140

Leu Thr Leu Leu Ile Leu Ala Leu Ile Ser Leu Leu Gln Cys Ser Cys
145                 150                 155                 160

Tyr Leu Glu Arg His Gln Ala Gln Ile Asp His Tyr Leu Gly Leu Ala
                165                 170                 175

Asn Lys Asn Val Lys Asp Ala Met Ala Lys Ile Gln Ala Lys Ile Pro
            180                 185                 190

Gly Leu Lys Arg Lys Ala Glu
        195
```

<210> SEQ ID NO 12
<211> LENGTH: 1862
<212> TYPE: DNA
<213> ORGANISM: Homo sapiens
<220> FEATURE:
<221> NAME/KEY: CDS
<222> LOCATION: (91)..(1647)

```
<400> SEQUENCE: 12
ggccgctgaa tggccgagtc gctgagccgc ggctgccgga cgggacggga ccggctaggc        60
tgggcgcgcc ccccgggccc cgccgtgggc atg ggc gca ctg gcc cgg gcg ctg       114
                                 Met Gly Ala Leu Ala Arg Ala Leu
                                   1               5 ctg ctg cct ctg ctg gcc cag tgg ctc ctg cgc gcc gcc ccg gag ctg        162
Leu Leu Pro Leu Leu Ala Gln Trp Leu Leu Arg Ala Ala Pro Glu Leu
         10                  15                  20 gcc ccc gcg ccc ttc acg ctg ccc ctc cgg gtg gcc gcg gcc acg aac        210
Ala Pro Ala Pro Phe Thr Leu Pro Leu Arg Val Ala Ala Ala Thr Asn
 25                  30                  35                  40 cgc gta gtt gcg ccc acc ccg gga ccc ggg acc cct gcc gag cgc cac        258
Arg Val Val Ala Pro Thr Pro Gly Pro Gly Thr Pro Ala Glu Arg His
                     45                  50                  55 gcc gac ggc ttg gcg ctc gcc ctg gag cct gcc ctg gcg tcc ccc gcg        306
Ala Asp Gly Leu Ala Leu Ala Leu Glu Pro Ala Leu Ala Ser Pro Ala
         60                  65                  70 ggc gcc gcc aac ttc ttg gcc atg gta gac aac ctg cag ggg gac tct        354
Gly Ala Ala Asn Phe Leu Ala Met Val Asp Asn Leu Gln Gly Asp Ser
 75                  80                  85 ggc cgc ggc tac tac ctg gag atg ctg atc ggg acc ccc ccg cag aag        402
Gly Arg Gly Tyr Tyr Leu Glu Met Leu Ile Gly Thr Pro Pro Gln Lys
         90                  95                 100 cta cag att ctc gtt gac act gga agc agt aac ttt gcc gtg gca gga        450
Leu Gln Ile Leu Val Asp Thr Gly Ser Ser Asn Phe Ala Val Ala Gly
105                 110                 115                 120 acc ccg cac tcc tac ata gac acg tac ttt gac aca gag agg tct agc        498
Thr Pro His Ser Tyr Ile Asp Thr Tyr Phe Asp Thr Glu Arg Ser Ser
                    125                 130                 135 aca tac cgc tcc aag ggc ttt gac gtc aca gtg aag tac aca caa gga        546
Thr Tyr Arg Ser Lys Gly Phe Asp Val Thr Val Lys Tyr Thr Gln Gly
            140                 145                 150 agc tgg acg ggc ttc gtt ggg gaa gac ctc gtc acc atc ccc aaa ggc        594
Ser Trp Thr Gly Phe Val Gly Glu Asp Leu Val Thr Ile Pro Lys Gly
        155                 160                 165 ttc aat act tct ttt ctt gtc aac att gcc act att ttt gaa tca gag        642
Phe Asn Thr Ser Phe Leu Val Asn Ile Ala Thr Ile Phe Glu Ser Glu
    170                 175                 180 aat ttc ttt ttg cct ggg att aaa tgg aat gga ata ctt ggc cta gct        690
Asn Phe Phe Leu Pro Gly Ile Lys Trp Asn Gly Ile Leu Gly Leu Ala
185                 190                 195                 200 tat gcc aca ctt gcc aag cca tca agt tct ctg gag acc ttc ttc gac        738
Tyr Ala Thr Leu Ala Lys Pro Ser Ser Ser Leu Glu Thr Phe Phe Asp
                    205                 210                 215 tcc ctg gtg aca caa gca aac atc ccc aac gtt ttc tcc atg cag atg        786
Ser Leu Val Thr Gln Ala Asn Ile Pro Asn Val Phe Ser Met Gln Met
                220                 225                 230 tgt gga gcc ggc ttg ccc gtt gct gga tct ggg acc aac gga ggt agt        834
Cys Gly Ala Gly Leu Pro Val Ala Gly Ser Gly Thr Asn Gly Gly Ser
            235                 240                 245 ctt gtc ttg ggt gga att gaa cca agt ttg tat aaa gga gac atc tgg        882
Leu Val Leu Gly Gly Ile Glu Pro Ser Leu Tyr Lys Gly Asp Ile Trp
        250                 255                 260 tat acc cct att aag gaa gag tgg tac tac cag ata gaa att ctg aaa        930
Tyr Thr Pro Ile Lys Glu Glu Trp Tyr Tyr Gln Ile Glu Ile Leu Lys
265                 270                 275                 280 ttg gaa att gga ggc caa agc ctt aat ctg gac tgc aga gag tat aac        978
Leu Glu Ile Gly Gly Gln Ser Leu Asn Leu Asp Cys Arg Glu Tyr Asn
                    285                 290                 295
```

```
gca gac aag gcc atc gtg gac agt ggc acc acg ctg ctg cgc ctg ccc       1026
Ala Asp Lys Ala Ile Val Asp Ser Gly Thr Thr Leu Leu Arg Leu Pro
            300                 305                 310 cag aag gtg ttt gat gcg gtg gtg gaa gct gtg gcc cgc gca tct ctg       1074
Gln Lys Val Phe Asp Ala Val Val Glu Ala Val Ala Arg Ala Ser Leu
    315                 320                 325 att cca gaa ttc tct gat ggt ttc tgg act ggg tcc cag ctg gcg tgc       1122
Ile Pro Glu Phe Ser Asp Gly Phe Trp Thr Gly Ser Gln Leu Ala Cys
330                 335                 340 tgg acg aat tcg gaa aca cct tgg tct tac ttc cct aaa atc tcc atc       1170
Trp Thr Asn Ser Glu Thr Pro Trp Ser Tyr Phe Pro Lys Ile Ser Ile
345                 350                 355                 360 tac ctg aga gac gag aac tcc agc agg tca ttc cgt atc aca atc ctg       1218
Tyr Leu Arg Asp Glu Asn Ser Ser Arg Ser Phe Arg Ile Thr Ile Leu
                365                 370                 375 cct cag ctt tac att cag ccc atg atg ggg gcc ggc ctg aat tat gaa       1266
Pro Gln Leu Tyr Ile Gln Pro Met Met Gly Ala Gly Leu Asn Tyr Glu
            380                 385                 390 tgt tac cga ttc ggc att tcc cca tcc aca aat gcg ctg gtg atc ggt       1314
Cys Tyr Arg Phe Gly Ile Ser Pro Ser Thr Asn Ala Leu Val Ile Gly
        395                 400                 405 gcc acg gtg atg gag ggc ttc tac gtc atc ttc gac aga gcc cag aag       1362
Ala Thr Val Met Glu Gly Phe Tyr Val Ile Phe Asp Arg Ala Gln Lys
410                 415                 420 agg gtg ggc ttc gca gcg agc ccc tgt gca gaa att gca ggt gct gca       1410
Arg Val Gly Phe Ala Ala Ser Pro Cys Ala Glu Ile Ala Gly Ala Ala
425                 430                 435                 440 gtg tct gaa att tcc ggg cct ttc tca aca gag gat gta gcc agc aac       1458
Val Ser Glu Ile Ser Gly Pro Phe Ser Thr Glu Asp Val Ala Ser Asn
                445                 450                 455 tgt gtc ccc gct cag tct ttg agc gag ccc att ttg tgg att gtg tcc       1506
Cys Val Pro Ala Gln Ser Leu Ser Glu Pro Ile Leu Trp Ile Val Ser
            460                 465                 470 tat gcg ctc atg agc gtc tgt gga gcc atc ctc ctt gtc tta atc gtc       1554
Tyr Ala Leu Met Ser Val Cys Gly Ala Ile Leu Leu Val Leu Ile Val
        475                 480                 485 ctg ctg ctg ctg ccg ttc cgg tgt cag cgt cgc ccc cgt gac cct gag       1602
Leu Leu Leu Leu Pro Phe Arg Cys Gln Arg Arg Pro Arg Asp Pro Glu
490                 495                 500 gtc gtc aat gat gag tcc tct ctg gtc aga cat cgc tgg aaa tga            1647
Val Val Asn Asp Glu Ser Ser Leu Val Arg His Arg Trp Lys
505                 510                 515 atagccaggc tgacctcaa gcaaccatga actcagctat taagaaaatc acatttccag       1707
ggcagcagcc gggatcgatg gtggcgcttt tcctgtgcc cacccgtctt caatctctgt       1767
tctgctccca gatgccttct agattcactg tcttttgatt cttgattttc aagctttcaa     1827
atcctcccta cttccaagaa aaaaaaaaaa aaaaa                                1862
```

<210> SEQ ID NO 13
<211> LENGTH: 518
<212> TYPE: PRT
<213> ORGANISM: Homo sapiens

<400> SEQUENCE: 13

```
Met Gly Ala Leu Ala Arg Ala Leu Leu Leu Pro Leu Leu Ala Gln Trp
1               5                   10                  15

Leu Leu Arg Ala Ala Pro Glu Leu Ala Pro Ala Pro Phe Thr Leu Pro
            20                  25                  30
```

```
Leu Arg Val Ala Ala Ala Thr Asn Arg Val Val Ala Pro Thr Pro Gly
        35                  40                  45

Pro Gly Thr Pro Ala Glu Arg His Ala Asp Gly Leu Ala Leu Ala Leu
50                  55                  60

Glu Pro Ala Leu Ala Ser Pro Ala Gly Ala Ala Asn Phe Leu Ala Met
65                  70                  75                  80

Val Asp Asn Leu Gln Gly Asp Ser Gly Arg Gly Tyr Tyr Leu Glu Met
                85                  90                  95

Leu Ile Gly Thr Pro Pro Gln Lys Leu Gln Ile Leu Val Asp Thr Gly
            100                 105                 110

Ser Ser Asn Phe Ala Val Ala Gly Thr Pro His Ser Tyr Ile Asp Thr
            115                 120                 125

Tyr Phe Asp Thr Glu Arg Ser Ser Thr Tyr Arg Ser Lys Gly Phe Asp
        130                 135                 140

Val Thr Val Lys Tyr Thr Gln Gly Ser Trp Thr Gly Phe Val Gly Glu
145                 150                 155                 160

Asp Leu Val Thr Ile Pro Lys Gly Phe Asn Thr Ser Phe Leu Val Asn
                165                 170                 175

Ile Ala Thr Ile Phe Glu Ser Glu Asn Phe Phe Leu Pro Gly Ile Lys
            180                 185                 190

Trp Asn Gly Ile Leu Gly Leu Ala Tyr Ala Thr Leu Ala Lys Pro Ser
        195                 200                 205

Ser Ser Leu Glu Thr Phe Phe Asp Ser Leu Val Thr Gln Ala Asn Ile
    210                 215                 220

Pro Asn Val Phe Ser Met Gln Met Cys Gly Ala Gly Leu Pro Val Ala
225                 230                 235                 240

Gly Ser Gly Thr Asn Gly Gly Ser Leu Val Leu Gly Gly Ile Glu Pro
                245                 250                 255

Ser Leu Tyr Lys Gly Asp Ile Trp Tyr Thr Pro Ile Lys Glu Glu Trp
            260                 265                 270

Tyr Tyr Gln Ile Glu Ile Leu Lys Leu Glu Ile Gly Gly Gln Ser Leu
        275                 280                 285

Asn Leu Asp Cys Arg Glu Tyr Asn Ala Asp Lys Ala Ile Val Asp Ser
    290                 295                 300

Gly Thr Thr Leu Leu Arg Leu Pro Gln Lys Val Phe Asp Ala Val Val
305                 310                 315                 320

Glu Ala Val Ala Arg Ala Ser Leu Ile Pro Glu Phe Ser Asp Gly Phe
                325                 330                 335

Trp Thr Gly Ser Gln Leu Ala Cys Trp Thr Asn Ser Glu Thr Pro Trp
            340                 345                 350

Ser Tyr Phe Pro Lys Ile Ser Ile Tyr Leu Arg Asp Glu Asn Ser Ser
        355                 360                 365

Arg Ser Phe Arg Ile Thr Ile Leu Pro Gln Leu Tyr Ile Gln Pro Met
    370                 375                 380

Met Gly Ala Gly Leu Asn Tyr Glu Cys Tyr Arg Phe Gly Ile Ser Pro
385                 390                 395                 400

Ser Thr Asn Ala Leu Val Ile Gly Ala Thr Val Met Glu Gly Phe Tyr
                405                 410                 415

Val Ile Phe Asp Arg Ala Gln Lys Arg Val Gly Phe Ala Ala Ser Pro
            420                 425                 430

Cys Ala Glu Ile Ala Gly Ala Ala Val Ser Glu Ile Ser Gly Pro Phe
        435                 440                 445

Ser Thr Glu Asp Val Ala Ser Asn Cys Val Pro Ala Gln Ser Leu Ser
```

-continued

```
        450                 455                 460
Glu Pro Ile Leu Trp Ile Val Ser Tyr Ala Leu Met Ser Val Cys Gly
465                 470                 475                 480

Ala Ile Leu Leu Val Leu Ile Val Leu Leu Leu Pro Phe Arg Cys
                485                 490                 495

Gln Arg Arg Pro Arg Asp Pro Glu Val Val Asn Asp Glu Ser Ser Leu
                500                 505                 510

Val Arg His Arg Trp Lys
            515
```